United States Patent
Riza

[19]

[11] Patent Number: 5,843,122
[45] Date of Patent: Dec. 1, 1998

[54] SURGICAL TOOL WITH PAIR OF PIVOTABLE JAWS

[76] Inventor: Erol D. Riza, 550 Riverside Dr., Rossford, Ohio 43460

[21] Appl. No.: 940,487

[22] Filed: Sep. 30, 1997

Related U.S. Application Data

[60] Division of Ser. No. 582,095, Jan. 2, 1996, Pat. No. 5,782,749, which is a continuation-in-part of Ser. No. 241,035, May 10, 1994, Pat. No. 5,480,409.

[51] Int. Cl.⁶ .................................................. A61B 17/28
[52] U.S. Cl. ............................................................. 606/207
[58] Field of Search ............................... 600/564; 606/51, 606/52, 136, 137, 167, 174, 175, 184, 185, 205, 206, 207, 208

[56] References Cited

U.S. PATENT DOCUMENTS

| | | |
|---|---|---|
| 1,274,669 | 8/1918 | Bohn . |
| 3,302,648 | 2/1967 | Nelson ..................... 606/208 |
| 3,735,763 | 5/1973 | Shannon et al. .......... 606/208 |
| 4,657,016 | 4/1987 | Garito et al. ................ 606/51 |
| 5,234,460 | 8/1993 | Stouder, Jr. . |
| 5,275,608 | 1/1994 | Forman et al. . |

FOREIGN PATENT DOCUMENTS

| | | |
|---|---|---|
| A-0541930 | 5/1991 | European Pat. Off. . |
| A00623316 | 11/1994 | European Pat. Off. . |
| 9320340 U | 7/1994 | Germany . |
| 9418094 U | 1/1995 | Germany . |
| WO-A-9312722 | 7/1993 | WIPO . |

*Primary Examiner*—William E. Kamm
*Attorney, Agent, or Firm*—MacMillan, Sobanski & Todd, LLC

[57] ABSTRACT

A surgical instrument tool including a tubular body having axially extending, diametrically opposed first and second yoke arms formed thereon. The first and second yoke arms each have a respective pivot hole formed therethrough. The tool further including a first jaw having a flange portion formed at one end thereof. The flange portion has first and second opposed faces, and a recess formed in the first face of the flange portion. A first pivot pin extends perpendicularly from the second face of the flange portion of the first jaw through the pivot hole in the first yoke arm to pivotally mount the first jaw on the body. The tool further including a second jaw having a flange portion formed at one end thereof. The flange portion has first and second opposed faces and a connector pin extending perpendicularly from the first face of the flange portion of the second jaw. The connector pin extends into the recess formed in the first face of the flange portion of the first jaw to pivotally couple the first and second jaws. A second pivot pin extends perpendicularly from the second face of the flange portion of the second jaw through the pivot hole in the second yoke arm to pivotally mount the second jaw on the body.

17 Claims, 13 Drawing Sheets

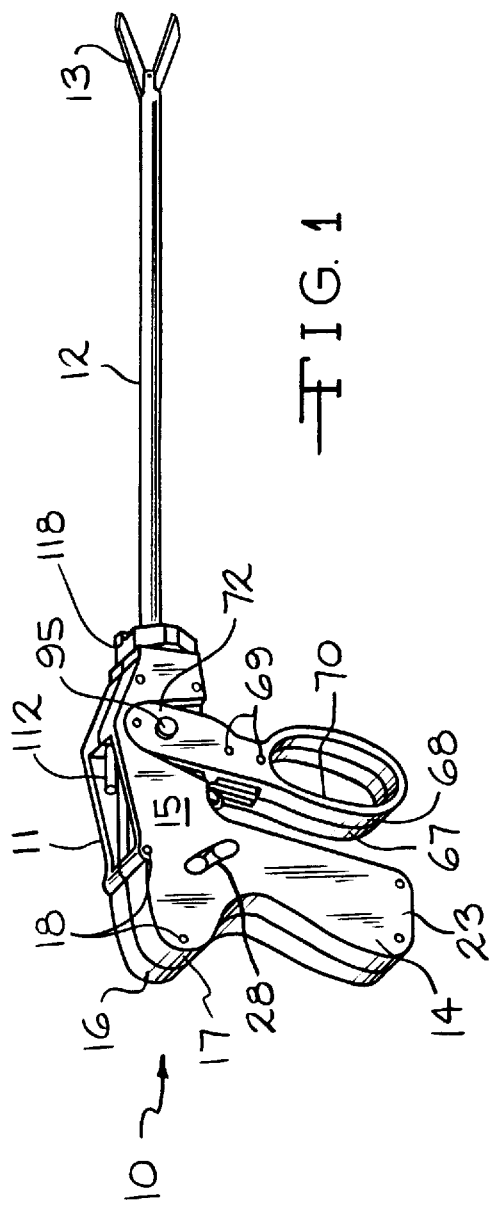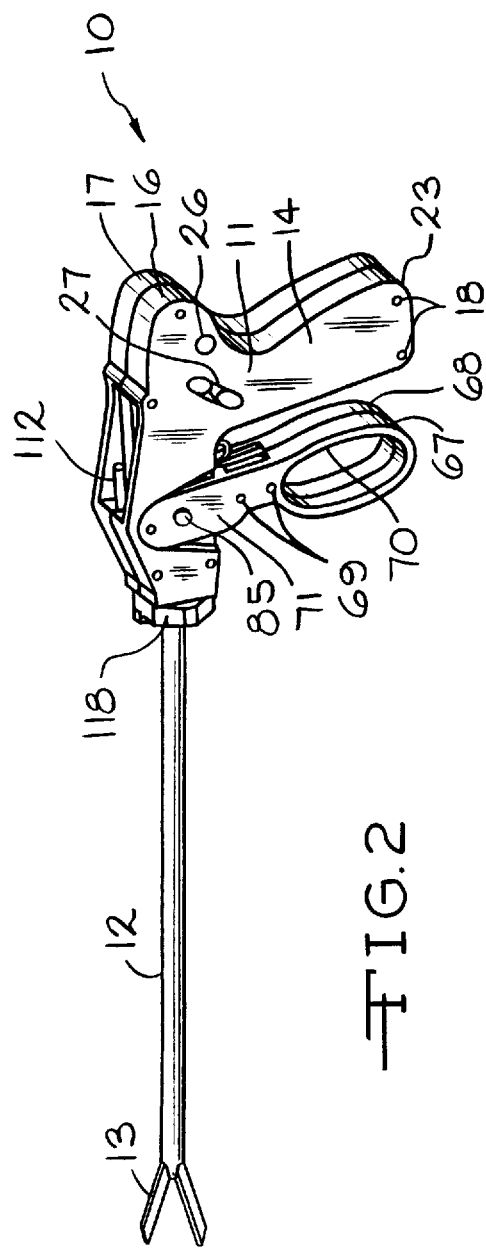

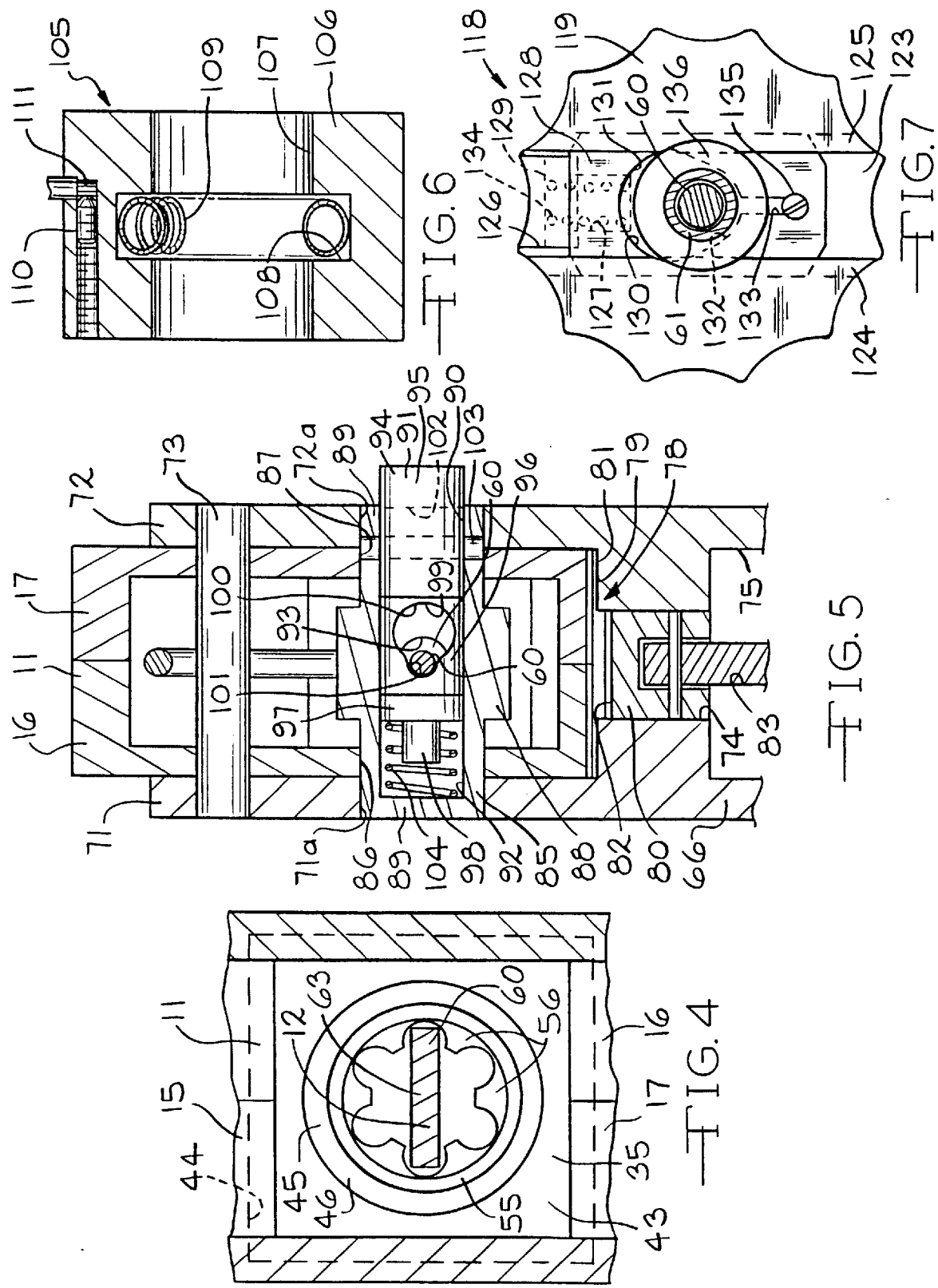

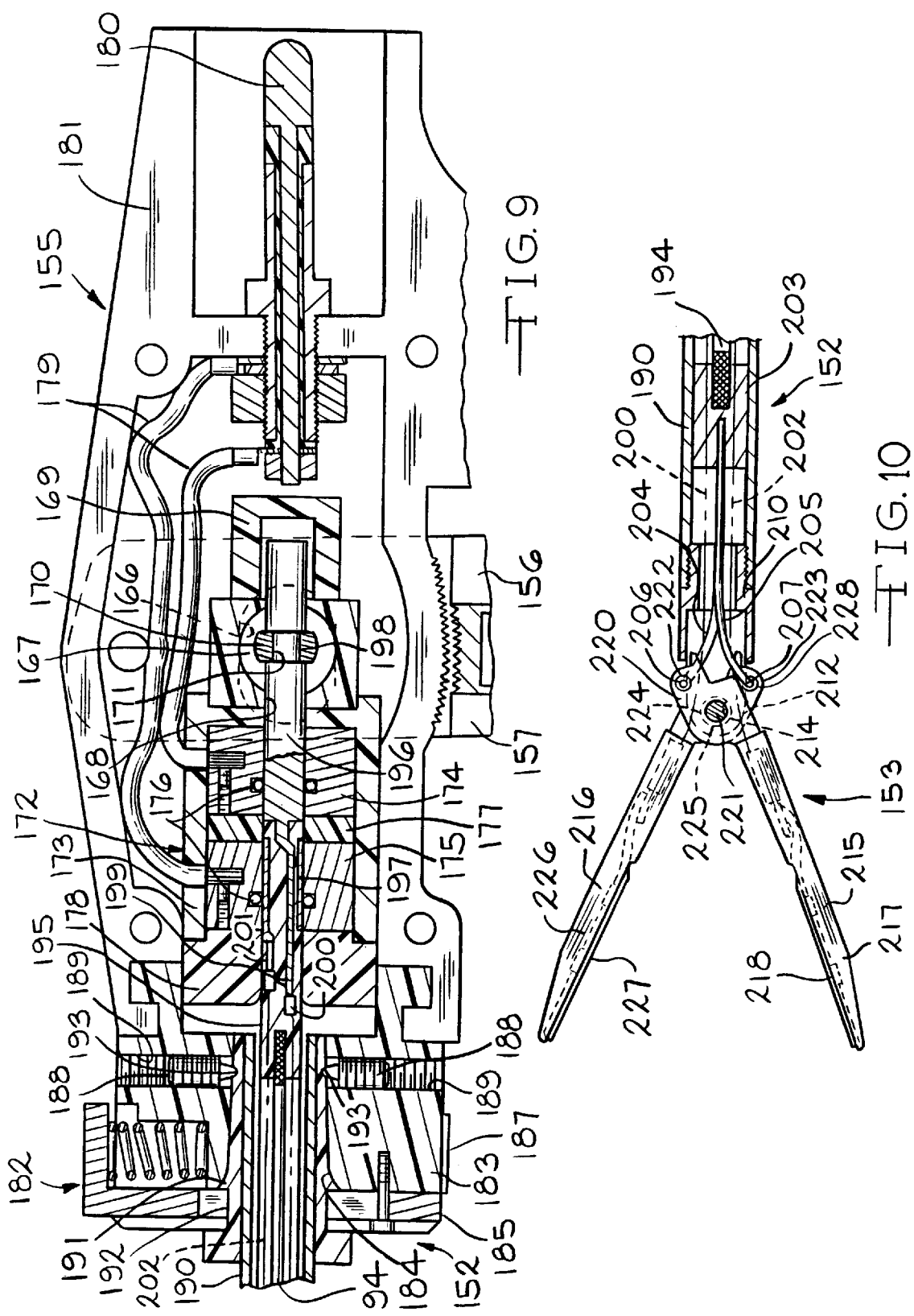

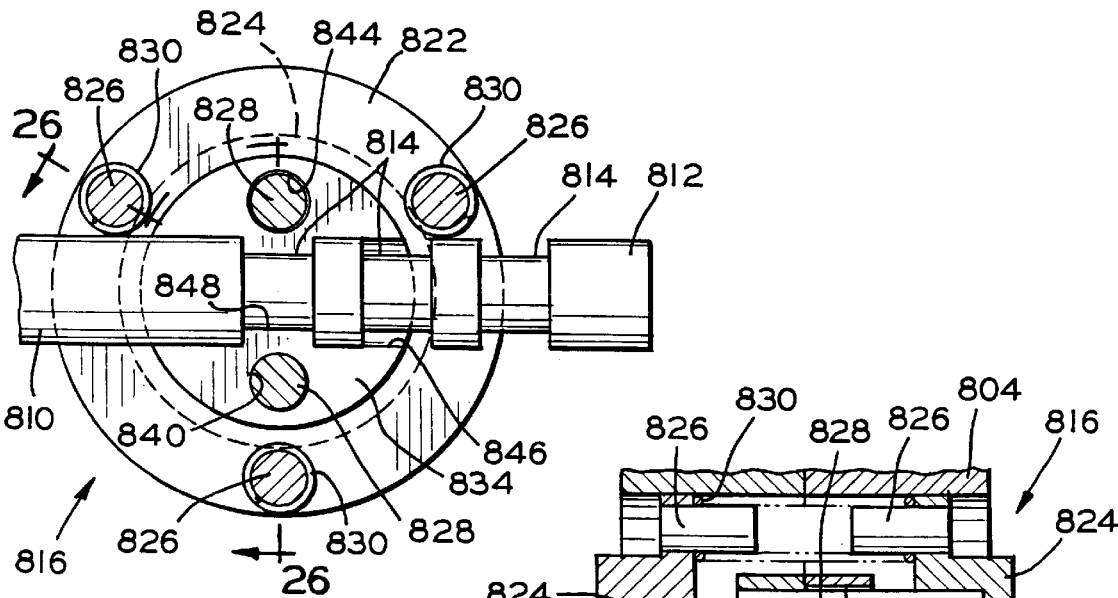
FIG. 25
FIG. 26
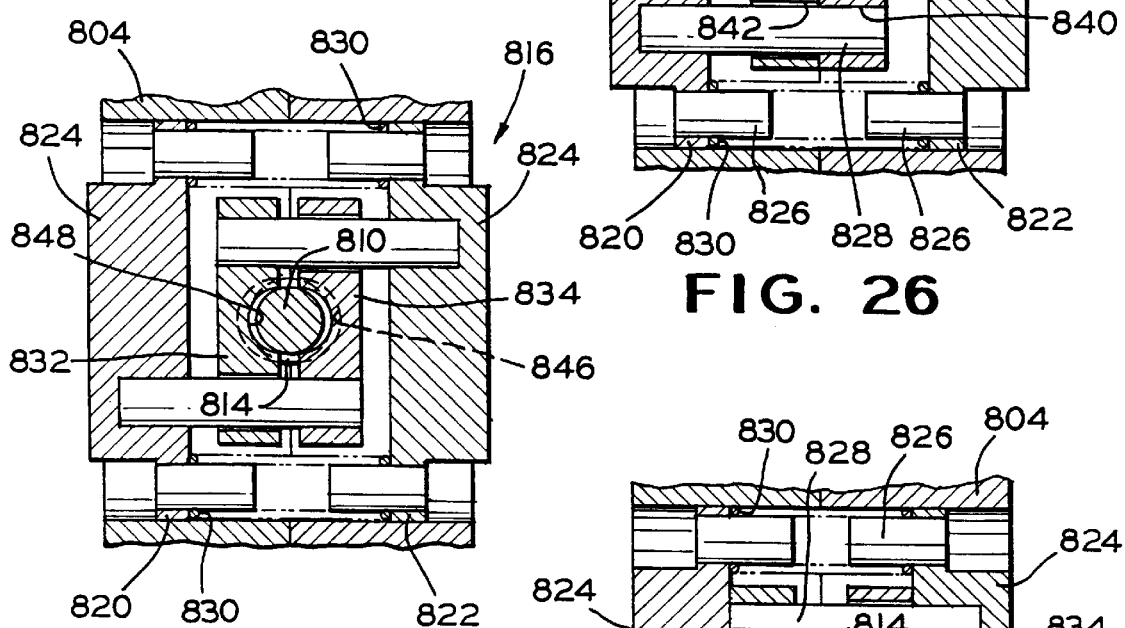
FIG. 27
FIG. 28

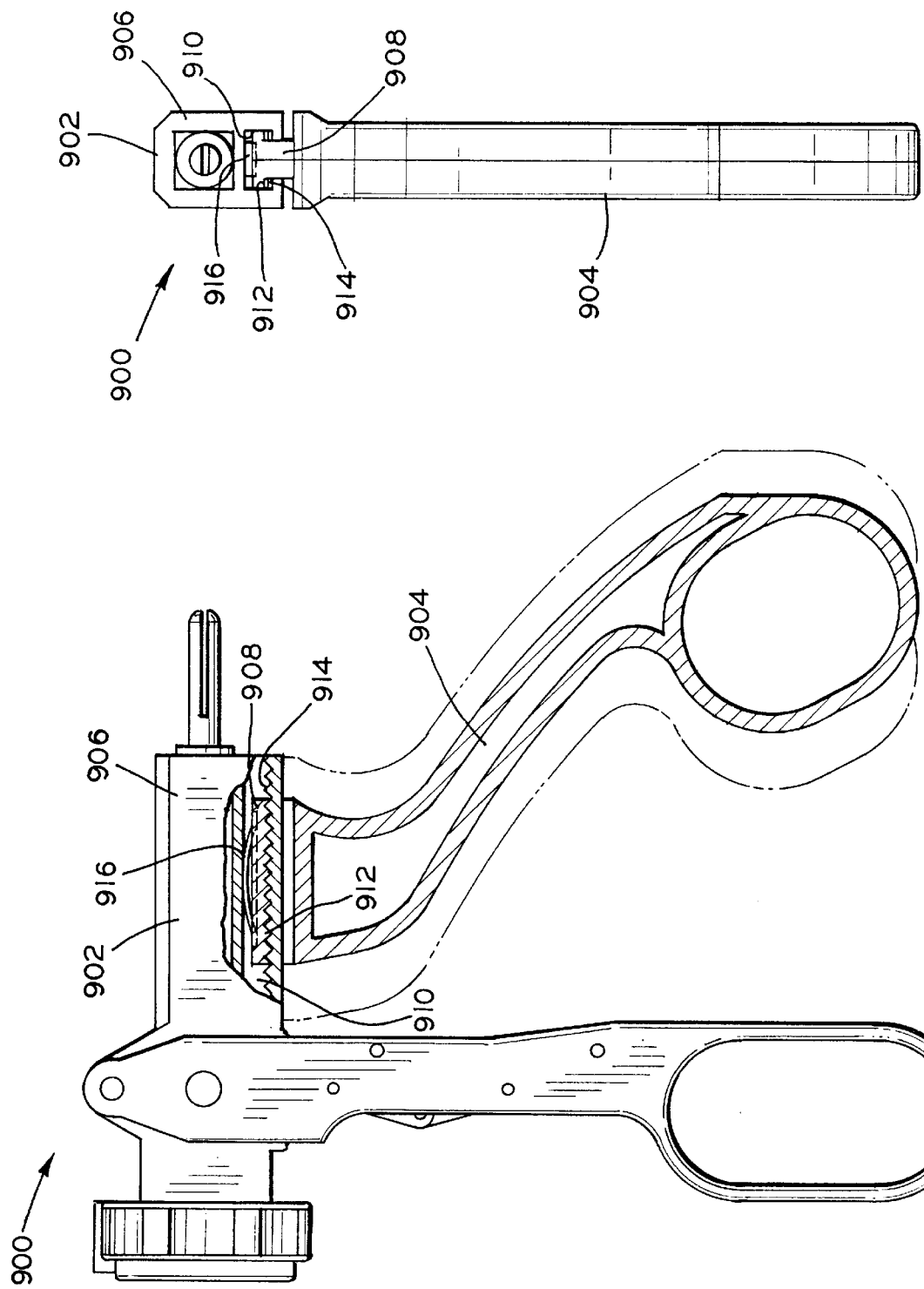

SURGICAL TOOL WITH PAIR OF PIVOTABLE JAWS

CROSS REFERENCE TO RELATED APPLICATION

This application is a divisional of application Ser. No. 08/582,095, filed Jan. 2, 1996, now U.S. Pat. No. 5,782,749, which is a continuation-in-part of application Ser. No. 08/241,035, filed May 10, 1994, now U.S. Pat. No. 5,480,409.

BACKGROUND OF THE INVENTION

This invention relates in general to surgical instruments and in particular to an improved structure for a laparoscopic surgical instrument.

Laparoscopic surgery is a relatively new operating technique which is much less invasive than conventional surgery and, therefore, may be performed using only a local anesthetic. Such laparoscopic surgery involves puncturing a relatively small opening through the abdominal wall and introducing an inert gas within the abdomen. The introduction of the inert gas expands the abdomen to facilitate access to the body parts requiring surgery and visual observation of the procedure. A hollow cylindrical tube is inserted into the puncture and is subsequently used as a conduit through which one or more elongated surgical instruments may be inserted within the abdomen. If desired, a plurality of such relatively small punctures may be formed through the abdominal wall to facilitate the use of several surgical instruments.

A number of laparoscopic surgical instruments are known in the art for use in laparoscopic surgical procedures. Although they vary widely in structure and operation, such laparoscopic surgical instruments generally include three basic components. First, a typical laparoscopic surgical instrument includes a handle which is grasped and manipulated by the user. The handle may be designed in the general hand of the user. Alternatively, the handle may be designed in the general shape of a hypodermic needle grip for engagement only by the thumb and fingers of the user. In either event, the handle usually includes one or more movable components which can be manipulated by the user for a purpose described below.

Second, a typical laparoscopic surgical instrument includes an elongated shaft portion which extends from the handle. The elongated shaft portion is provided for extending through the hollow cylindrical tube discussed above during the laparoscopic surgical operation. The elongated shaft portion may include an actuator member which is connected for movement or other operation with the movable component of the handle.

Third, a typical laparoscopic surgical instrument includes a tool portion mounted on the end of the elongated shaft portion. The tool portion is connected to the actuator member of the elongated shaft portion such that movement of the movable component of the handle causes operation of the tool portion.

As mentioned above, a number of laparoscopic surgical instruments of this general type are known in the art. In some of such known laparoscopic surgical instruments, the associated tool portions may be rotated relative to the handle to a desired orientation by manually rotating a thumbwheel fixed to the associated shaft portions. It would be desirable to provide an improved structure for a laparoscopic surgical instrument of this general type that can be motorized to facilitate the use thereof. Additionally, in other ones of such known laparoscopic surgical instruments, the elongated shaft portions and associated tool portions are permanently secured to the handle. Thus, the entire laparoscopic surgical instrument must be sterilized or disposed of after use. It would also be desirable to provide an improved structure for a laparoscopic surgical instrument of this general type in which the elongated shaft portion and associated tool portion are removable from the handle. This will allow the relatively inexpensive elongated shaft portion and associated tool portion to be disposed of after use, while allowing the relatively expensive handle to be sterilized and reused.

SUMMARY OF THE INVENTION

This invention relates to a surgical instrument including a handle adapted to releasably engage a shaft portion mounting a tool having relatively moveable parts. The handle is provided with an actuating structure which includes a trigger arm selectively moveable relative to the handle to cause concurrent movement of the relatively moveable parts of the tool. The actuating structure may include a locking mechanism for releasably fixing the position of the handle relative to the handle, thus releasably fixing the relative positions of the moveable parts of the tool. The handle is also provided with an operating mechanism which is operatively coupled to the tool to selectively rotate the tool relative to the handle. The operating mechanism may be motorized. The operating mechanism may include a control circuit which can be programmed to activate the motor to rotate the tool through specific intervals of displacement is a chosen direction according to selective manipulations of control switches. Various objects and advantages of this invention will become apparent to those skilled in the art from the following detailed description of the preferred embodiment, when read in light of the accompanying drawings.

BRIEF DESCRIPTION OF THE DRAWINGS

FIG. 1 is a perspective view of a laparoscopic surgical instrument in accordance with this invention showing a first side thereof.

FIG. 2 is another perspective view of the instrument illustrated in FIG. 1, showing a second side thereof.

FIG. 4 is an enlarged elevational view, partly in section, taken along the line 4—4 of FIG. 3.

FIG. 5 is an enlarged elevational view, partly in section, taken along the line 5—5 of FIG. 3.

FIG. 6 is an enlarged view of the contact shown in FIG. 3.

FIG. 7 is an enlarged elevational view, partly in section, taken along the line 7—7 of FIG. 3.

FIG. 9 is an enlarged elevational view, partly in section, of the receiver portion shown in FIG. 8.

FIG. 10 is an enlarged elevational view, partly in section, of the tool of the instrument shown in FIG. 8.

FIG. 25 is an enlarged view of the locking mechanism illustrated in FIG. 24.

FIG. 26 is a view taken along the line 26—26 of FIG. 25, showing the locking mechanism in a lock position.

FIG. 27 is a view similar to that of FIG. 26, showing the locking mechanism thereof in an intermediate position.

FIG. 28 is a view similar to that of FIG. 26, showing the locking mechanism thereof in an unlock position.

FIG. 29 is a side elevation view of a ninth embodiment of the instrument of this invention, showing a different structure for adjustably mounting the grip portion of the handle portion.

FIG. 30 is a proximal end view of the instrument shown in FIG. 29.

DETAILED DESCRIPTION OF THE PREFERRED EMBODIMENT

Figure 3:
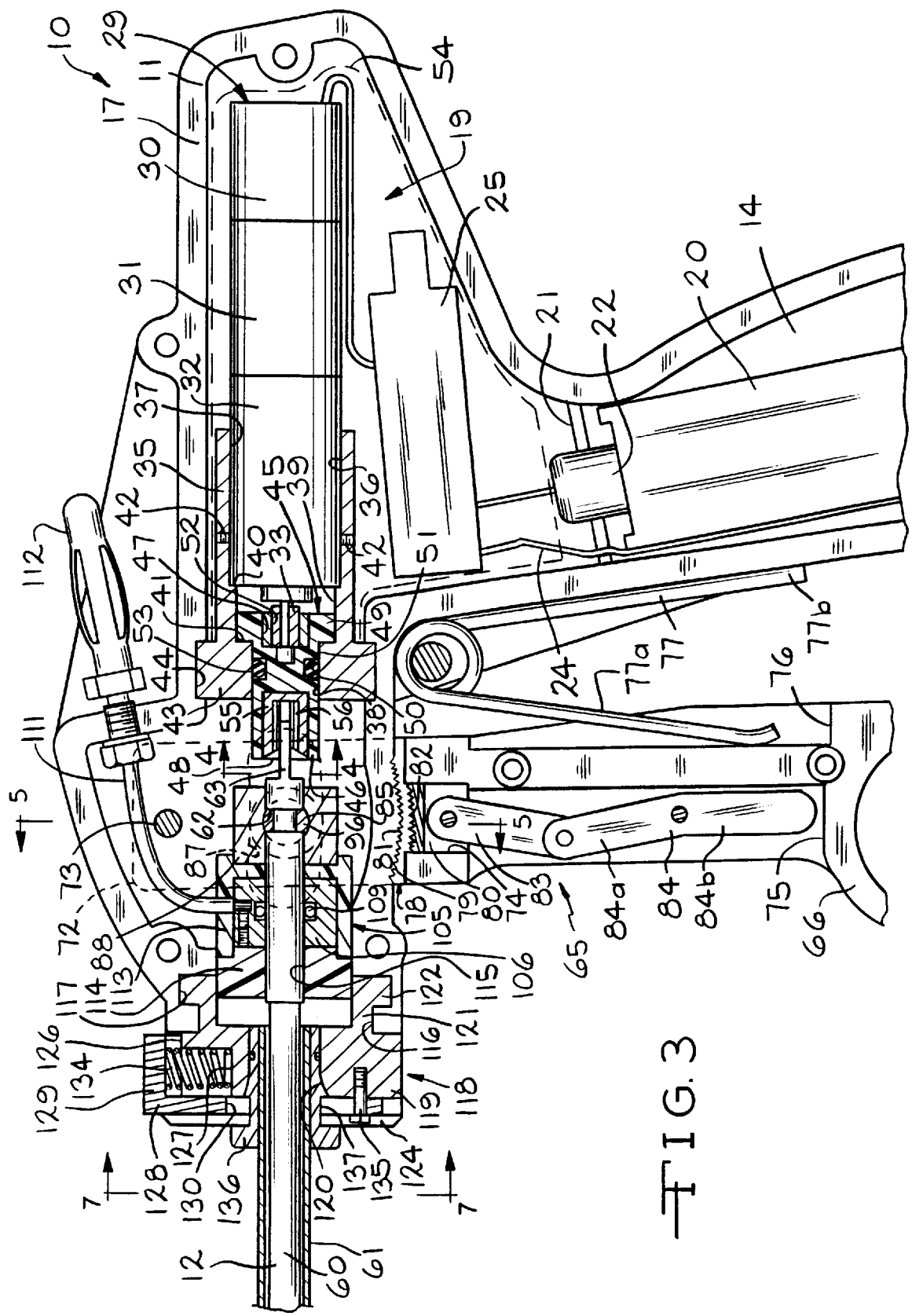
FIG. 3 is an enlarged fragmentary elevational view, partly in section, of the instrument illustrated in FIGS. 1 and 2, with one side piece of the handle removed to reveal the interior components thereof.

Referring now to the drawings, there is illustrated in FIGS. 1 through 3 a first embodiment of a laparoscopic surgical instrument, indicated generally at 10, in accordance with this invention. The instrument 10 includes a pistol-shaped handle 11, a shaft portion 12 which is releasably secured by the proximal end thereof to the handle 11, and a tool 13 secured to the distal end of the shaft portion 12, each of which will be described in greater detail below. As used in this application, "proximal" means that portion of the structure under discussion which is normally close to the user when the instrument 10 is in use. Similarly, "distal" refers to that portion of the structure under discussion which is farther away from the user holding the instrument 10.

The handle 11 includes a hollow pistol grip portion 14 on top of which integrally extends a hollow receiver portion 15. Preferably, the pistol-shaped handle 11 is made of two symmetrical side pieces 16 and 17, preferably molded of a plastic material, that are detachably connected by conventional means, such as screws 18. Each of the side pieces 16 and 17 define half of the grip portion 14 and half of the receiver portion 15. The side pieces 16 and 17 of the handle 11 are preferably formed of a material which can be repeatedly sterilized in a conventional manner without degrading the performance of the instrument 10.

It is anticipated that the handle 11 of the instrument 10 will frequently be grasped by the grip portion 14 such that the grip portion 14 extends generally downwardly toward the floor and the receiver portion 15 is disposed generally upwardly of the grip portion 14 and extends generally horizontally. Therefore, the terms "up", "down", "upper", and "lower", and terms of similar import used to describe the layout of the instrument 10 will be understood to refer to the instrument 10 while held in that orientation, although the instrument 10 may certainly be operated in other orientations.

As shown in FIG. 3, the handle 11 is sized and shaped to contain an operating mechanism 19 for actuating and rotating the tool 13. In the preferred embodiment, the portion of the operating mechanism 19 which rotates the tool 13 is powered by batteries 20 disposed within the grip portion 14. Lithium batteries are preferred for their relatively long shelf life and flat discharge characteristics. It has been estimated that two DL123A (3 volt, 1310 milliamp-hour) lithium batteries will operate the instrument 10 long enough to perform approximately one thousand typical surgical procedures, or approximately two years in normal use. Of course, other battery arrangements may be used. For example, a rechargeable battery may be utilized, and provided with an electrical plug molded through the grip portion 14 to permit recharging of the battery between uses of the instrument 10. Alternatively, the grip portion 14 may be provided with a window to permit easy access to relatively frequently replaced disposable batteries contained within the grip portion 14.

Each of the side pieces 16 and 17 is provided with a rib 21 (only the rib 21 on the side piece 17 is shown, in FIG. 3) extending transversely across the grip portion 14. The ribs 21 of the side pieces 16 and 17 mate to form a bulkhead separating the batteries 20 from the rest of the operating mechanism 19.

An electrical connector 22 is supported by the ribs 21. The connector 22 is electrically connected to and supports one end of the batteries 21. A second, similar connector (not shown) is supported by a similar set of ribs (also not shown) traversing a lower part 23 (FIGS. 1 and 2) of the grip portion 14. This second connector is electrically connected to and supports the other end of the batteries 20. An electrical conductor 24, electrically connected to the second connector, passes through the bulkhead formed by the ribs 21. The penetrations of the conductor 24 and the connector 22 through the bulkhead formed by the ribs 21 as well as the joint between the two opposed ribs 21 are substantially leak-tight, to protect the rest of the operating mechanism 19 in the event of leakage from the batteries 20.

The battery powered portion of the operating mechanism 19 is preferably regulated by a control circuit 25. The conductor 24 and the connector 22 are electrically connected to the control circuit 25, thereby connecting the batteries 20 as a power source to the control circuit 25. The control circuit 25 includes conventional low battery voltage detection circuitry (not shown) which controls the operation of a low battery indicating light 26 (FIG. 2) mounted on the side piece 16. Of course, although only a single low battery indicating light 26 is shown, a second low battery indicating 26 may be provided in the side piece 17, or the location of the low battery indicating light 26 moved to any desired location to provide ambidextrous indication of a discharged battery condition.

Commands to direct rotation of the tool 13 are input to the control circuit 25 by means of a pair of identical thumb switches 27 and 28 (FIGS. 1 and 2). The thumb switch 27 is mounted on the side piece 16 where it may be conveniently operated by the user's right thumb as the instrument 10 is held in the user's right hand (FIG. 2). Similarly, the thumb switch 28 is mounted on the side piece 17 where it may be conveniently operated by the user's left thumb as the instrument 10 is held in the user's left hand (FIG. 1), providing for ambidextrous operation of the instrument 10.

The thumb switches 27 and 28 are preferably of the conventional rocker switch type, in which single member, centrally pivoted, may have either end depressed to actuate a respective microswitch under the selected end. A microswitch which is believed to be suitable is available from C&K Switch of Newton, Mass. By actuating one of the microswitches of the thumb switch 27, the user can direct clockwise rotation of the tool 13; by actuating the other of the microswitches of the thumb switch 27, the user can direct counter-clockwise rotation of the tool 13. Similarly, the thumb switch 28 can be used to direct clockwise or counter-clockwise rotation of the tool 13.

The control circuit 25 preferably includes a programmable microprocessor to precisely regulate the operation of the operating mechanism 19 in response to engagement of the thumb switches 27 and 28. For example, the microprocessor may be programmed to cause the operating mechanism 19 to rotate the tool 13 continuously in the clockwise direction while a first one of the microswitches of the thumb switch 27 is actuated, stopping the tool 13 when the thumb switch 27 is released. The microprocessor can be programmed to rotate the tool 13 continuously in the counter-clockwise direction while the other one of the microswitches of the thumb switch 27 is depressed, stopping if the thumb switch 27 is released or after the tool 13 has rotated a first predetermined amount (such as 360°).

Preferably the microprocessor in the control circuit 25 will be programmed to respond to the thumb switch 28 in a manner similar to that programmed for the thumb switch 27. In one suitable ergonomic arrangement, the thumb switches 27 and 28 will be connected to the control circuit 25 such that actuation of the upper microswitch of the thumb switch 27 or the lower microswitch of the thumb switch 28 will result in clockwise rotation of the tool 13. Similarly, actuation of the upper microswitch of the thumb switch 28 or the lower microswitch of the thumb switch 27 will, result in counter-clockwise rotation of the tool 13. Of course, those of ordinary skill in the art will recognize that the microprocessor of the control circuit 25 may be programmed to control the rotation of the tool 13 in a variety of ways in response to actuation and release of the thumb switches 27 and 28. For an additional example, it is contemplated that the control circuit 25 can be caused to keep track of the number of times a thumb switch 27 or 28 is actuated within a predetermined period of time, and vary control of the tool 13 in response thereto.

The output of the control circuit 25 is directed to a conventional motor assembly 29. The motor assembly 29 includes an encoder 30, a motor 31 and a set of reduction gears 32. A motor assembly which is believed to be suitable is available as Model No. 1219E006GK380 from Micro Mo Electronics, Inc., of St. Petersburg, Fla. An output member 33 is pressed onto, or otherwise suitably secured to the output shaft of the reduction gears 32 of the motor assembly 29. In the preferred embodiment, the output member 33 has a generally oval cross-section. The purpose of the output member 33 will be explained below.

The motor assembly 29 is supported within a tubular support 35. An axial bore 3 6 is defined through the support 35. A proximal portion 37 of the bore 36 defines a relatively large diameter. A distal portion 38 of the bore 36 defines a relatively small diameter. An intermediate portion 39 is defined between the proximal portion 37 and the distal portion 38, and defines a diameter which is smaller than that of the proximal portion 37 but larger than that of the distal portion 38. Thus, a first shoulder 40 is defined between the proximal portion 37 and the intermediate portion 39 of the bore 36. A second shoulder 41 is defined between the intermediate portion 39 and the distal portion 38 of the bore 36. The distal end of the motor assembly 29 is mounted within the proximal portion 37 of the bore 36 with the distal end of the motor assembly 29 abutting the first shoulder 40 within the bore 36 to axially position the motor assembly 29. A pair of opposed set screws 42, which are threaded into the support 35, engage the motor assembly 29 to retain the motor assembly 29 in the support 35 and to prevent the motor assembly 29 from rotating relative thereto.

The support 35 has an outwardly extending flange 43 at the distal end thereof. The flange 43, which has a rectangular cross-section, engages a mating recess 44 extending about the inner surface of the hollow receiver portion 15 of the handle 11, so that the support 35 is axially positioned and supported within the handle 11 (FIGS. 3 and 4). The receiver portion 15 of the handle 11 has a generally rectangular cross-section and thus engages the rectangular flange 43 to prevent rotation of the support 35 relative to the handle 11. Preferably the recess 44 provides a close fit with the flange 43, such that a moisture resistant seal is formed therebetween.

A generally cylindrical coupling 45 is provided to transmit torque from the output member 33 on the output shaft of the motor assembly 29 to the shaft portion 12 of the instrument 10. The coupling 45 includes a body 46 which is preferably molded of a plastic material which transmits torque well and, for reasons which will be discussed below, has good electrical insulation properties. The body 46 has a first axially extending recess 47 formed on the proximal end thereof, and has a second axially extending recess 48 formed on the distal end thereof. A radially outwardly extending flange 49 is formed on the proximal end of the body 45. A circumferential groove 50 is formed in the outer surface of the body 46, intermediate the flange 49 and the distal end of the body 46.

A hollow metallic insert 51 is preferably secured in the first recess 47. The insert 51 may be secured therein using any conventional means such as an adhesive, or molding the body 45 about the insert 51. The insert 51 has a cavity 52 adapted to receive the output member 33 of the motor assembly 29 to couple the output member 33 of the motor assembly 29 for rotation of the coupling 45.

The flange 49 is rotatable within the intermediate portion 39 of the bore 36 through the support 35. The flange 43 defines a diameter which is greater than the diameter of the distal portion 38 of the bore 36. Thus, the coupling 46 is prevented from moving away from the motor assembly 29 beyond a first axial position relative to the motor assembly by the second shoulder 41 of the support 35. The coupling 45 is prevented from moving toward the motor assembly 29 beyond a second axial position defined where the output member 33 bears against the bottom of the cavity 52 in the insert 51 in the proximal end of the coupling 45. The fit of the output member 33 within the cavity 52 in the insert 51 is such that the coupling 45 can move axially between the first and second axial positions relative to the motor assembly 29. The coupling 45 can thus rotate freely with the flange 49 thereof free to move axially to a position spaced slightly apart from the second shoulder 42 of the support 35.

An elastomeric O-ring 53 disposed in the groove 50 and bears against the distal portion of the bore 36 through the support 35, thereby providing a moisture resistant seal between the coupling 45 and the support 35. It will be appreciated that the O-ring, cooperating with the coupling 45 and the support 35 prevent passage of moisture from the distal end of the handle 11 to the proximal end thereof. Recalling the bulkhead formed by the cooperating ribs 21 formed on the side pieces 16 and 17, it will be further appreciated that the motor assembly 29 and the control circuit 25 are thus contained in a moisture-proof compartment. Thus, these electrical components are protected from the various fluids to which the instrument 10 may be exposed, such as during surgery and during sterilization. Additionally, the motor assembly 29 and control circuit 25 may be shielded against induced voltages from other electrical equipment or components which may be in use nearby. For example, the compartment in which the motor assembly 29 and control circuit 25 are contained may be lined with a conductive foil 54 (shown diagrammatically by a broken line in FIG. 3) to shield these components.

A metallic insert 55 is fixed in the recess 48 formed on the distal end of the coupling 45. As with the insert 51 in the recess 47, the insert 55 may be fixed in the recess 48 by conventional means. As seen in FIG. 4, the insert 55 is hollow and provided with inwardly extending splines 56, the purpose of which will be explained below.

Referring again to FIG. 3, the shaft portion 12 of the instrument 10 an inner rod or actuating member 60 which is moveable within an outer tube 61. A circumferential groove 62 is formed intermediate the proximal and distal ends of the actuating member 60, preferably near the proximal end thereof. The proximal end of the actuating member 60 is formed as an axially extending flat tongue 63. The tongue 63 extends within the insert 55 of the coupling 45, and engages the splines 56 therein. Thus, rotation of the coupling 45 by the motor assembly 29 causes the actuating member 60 of the shaft portion 12 of the instrument 10 to rotate. In the embodiment illustrated in FIGS. 1 and 2, the distal end of the actuating member 60 (not shown) is fixed to the tool 13 in a conventional manner. Thus, rotation of the actuating member 60 causes the tool 13 to rotate.

The operating mechanism 19 further includes an actuating structure 65 for moving the actuating member 60 axially relative to the tube 61, in order to actuate the tool 13. The actuating structure 65 can move the actuating member 60 only a relatively short distance. Such movement of the actuating member 60 relative to the coupling 45 is accommodated by movement of the tongue 63 forming the proximal end of the actuating member 60 relative to the splines 56 within the insert 55 in the coupling 45.

The actuating structure 65 includes a trigger arm 66. The trigger arm 66 which is preferably made from a plastic material, may be formed as a single piece, or, as is shown in FIGS. 1 and 2, formed from two mating portions 67 and 68 secured together by suitable conventional means, such as screws 69. In either case, the lower portion of the trigger arm 66 is provided with a finger grip 70 for actuating the trigger arm 66. The finger grip 70 is preferably formed as an elongate opening through the trigger arm to aid the user (not shown) in grasping the instrument 10.

The upper portion of the trigger arm 66 is formed as a yoke, having a pair of yoke arms 71 and 72 extend on either side of the receiver portion 15 of the handle 11 (as best seen by referring to FIGS. 1, 2, and 5). An aperture 71a is formed through the yoke arm 71. Similarly, an aperture 72a is formed through the yoke arm 72. The purpose of the apertures 71a and 72a will be explained below. A pin 73 extends between the yoke arms 71 and 72, and through the receiver portion 15 of the handle 11, to pivotally mount the trigger arm 66 on the handle 11 for movement relative thereto.

A bore 74 extends vertically through the upper portion of the trigger arm 66, extending from between the yoke arms 71 and 72 to a central recess 75 formed in the distal face of the trigger arm 66. A second central recess 76 is formed on the proximal face of the trigger arm 66. The purpose of the bore 74 and of the recesses 75 and 76 will be explained below.

A spring 77 or similar resilient structure is provided for urging the trigger arm 66 to a first position, relatively away from the grip portion 14 of the handle 11. The first position of the trigger arm 66 corresponds to the unactuated condition of the tool 13. As will be further explained below, when the trigger arm 66 is moved toward the handle 11 to a second position, the tool 13 is actuated. A pin extends between the side pieces 16 and 17, and through a loop in the spring 77 to retain the spring 77 in place relative to the handle 11. One arm 77a of the spring 77 is retained in the recess 76 formed in the proximal face of the trigger arm 66, and bears against the trigger arm 66. The other arm 77b of the spring 77 bears against the grip portion 14 of the handle 11.

The trigger arm 66 is provided with a releasable locking mechanism 78 for selectively retaining the trigger arm 66 (and thus the moveable portions of the tool 13) at substantially any selected position within the range of movement thereof. Preferably, the locking mechanism 78 is embodied as a surface feature forming a ratchet 79 and a pawl 80 which can easily engage and disengage the ratchet 79 to lock and unlock the instrument 10 as desired. The ratchet 79 is preferably formed as a series of laterally extending teeth 81 formed in a convex arc on the underside of the receiver portion 15 of the handle 11. However, it will be understood that other surface features, such as slots formed in the handle 11 may be suitably used. The pawl 80 is reciprocal in the bore 74 of the trigger arm 66 to selectively engage and disengage the ratchet 79. Preferably the upper surface of the pawl 80 is provided with a plurality of laterally extending teeth 82 arranged on a concave arc. This arcuate arrangement of the teeth 81 and 82 permits multiple teeth 82 of the pawl 80 to engage the teeth 81 of the ratchet 79 at any point in the travel of the trigger arm 66. Thus, multiple ones of the teeth 81 and 82 can share any loads which may be experienced.

The pawl 80 is pivotally connected to a toggle arm 83 which in turn is pivotally connected to a bell crank lever 84. The lever 84 has arms 84a and 84b formed at an angle to one another. The lever 84 is pivotally mounted within the recess 75 on the distal face of the trigger arm 66. The arm 84a of the lever 84 and the toggle arm 83 form a toggle joint such that if the user presses the arm 84a or the toggle arm 83 inwardly into the recess 75, the pawl 80 will be moved upwardly into engagement with the ratchet 79. The user presses the arm 84b inwardly into the recess 75 to cause the lever 84 to pivot the arm 84a outwardly. This in turn causes the toggle arm 83 to pull the pawl 80 out of engagement with the ratchet 79. Thus the user can selectively lock or unlock the trigger arm 66 in the first position thereof, the second position thereof, or at any intermediate position by pressing a finger against, respectively, the arm 84a or the arm 84b of the lever 84.

As most clearly shown in FIG. 5, a trunnion 85 extends between the yoke arms 71 and 72 of the trigger arm 66 and through openings 86 and 87 in, respectively, the side pieces 16 and 17 of the handle 11. As shown by the broken line in FIG. 3, the opening 87 in the side piece 17 is an elongated oval with sufficient clearance to accommodate the movement of the trunnion 85 as the trigger arm 66 is moved between the first and second positions thereof. The opening 86 in the side piece 16 has a similar shape.

The trunnion 85 includes a generally cubical receiver portion 88. The receiver portion 88 has a pair of relatively smaller cylindrical extensions 89 extending out of opposed faces. The extensions 89 extend through the openings 86 and 87 in the side pieces 16 and 17 to engage respective ones of the apertures 71a and 72a in the yoke arms 71 and 72 of the trigger arm 66. The lateral faces of the receiver portion 88 bear against the side pieces 16 and 17 to secure the trunnion 85 laterally relative to the receiver portion 15 of the handle 11. The trunnion 85 is provided with a first bore 90 extending from a first end 91 of the trunnion to a point adjacent a second end 92 of the trunnion. Thus the first bore 90 forms a recess in the first end 91 which extends more than half way, but not all the way, through the trunnion 85. Additionally, a second bore 93 extends horizontally through the middle of the trunnion 85 perpendicular to, and communicating with, the first bore 90. The actuating member 60 of the shaft portion 12 extends through the second bore 93.

A detent 94 is mounted for reciprocation in the first bore 90 in the trunnion 85. The detent 94 is generally cylindrical, and includes a first generally cylindrical bearing portion 95, a receiver portion 96 formed as a flat plate, a second cylindrical bearing portion 97, and a reduced diameter cylindrical guide portion 98. The bearing portions 95 and 97 slidingly engage the surface of the first bore 90 of the trunnion 85 to radially position the detent 94. A pear-shaped opening 99 is formed through the receiver portion 96 of the detent 94. The actuating member 60 extends through the pear-shaped opening 99. The pear-shaped opening 99 is oriented such that the larger diameter portion 100 thereof is closer to the first bearing portion 95 of the detent 94, and the smaller diameter portion 101 is closer to the second bearing portion 97 of the detent 94. The smaller diameter portion 101 of the pear-shaped opening 99 has a vertical diameter which is slightly greater than the diameter of the actuating member 60 at the base of the groove 62 therein, and less than the diameter of the actuating member 60 adjacent to the groove 62. The larger diameter portion 100 of the pear-shaped opening 99 has a vertical diameter which is slightly greater than the diameter of the actuating member 60 adjacent to the groove 62. Thus, when the detent 94 is positioned such that the actuating member 60 passes through the larger diameter portion 100 of the pear-shaped opening 99, the actuating member 60 may be moved axially relative to the detent 94. Thus the detent 94 is in a disengaged position. However, when the groove 62 in the actuating member 60 is aligned with the receiver portion 96 of the detent 94, the detent 94 may be moved laterally relative to the actuating member 60, such that the receiver portion 96 of the detent 94 engages the groove 62. When the actuating member 60 is thus engaged by the detent 94, the axial position of the actuating member 60 is fixed relative to the detent 94 within the trunnion 85. Thus, when the trunnion 85 is moved by the trigger arm 66 of the actuating structure 65, the actuating member 60 will move axially with the detent 94 within the trunnion 85. The detent 94 is thus in the engaged position.

It will be noted that the apertures 71a and 72a in respective yoke arms 71 and 72, are moved through an arc by the trigger arm 66, while the actuating member 60 to which the trunnion 85 is fixed reciprocates linearly. However, the arc of movement of the apertures 71a and 72a is relatively short, so that little change in vertical position occurs. What little vertical displacement of the trunnion 85 which would otherwise occur is accommodated by sizing the apertures 71a and 72a to receive the trunnion 85 with a relatively loose fit.

A vertical bore 102 is formed through the first bearing portion 95 of the detent 94. A pin 103 extends through the bore 102, and is fixed at either end thereof in the cylindrical extension 89 at the first end 91 of the trunnion 85. The bore 102 is laterally elongated, thus permitting the detent 94 to be reciprocated within the first bore 90 of the trunnion 85. However, the pin 103 through the bore 102 prevents the detent 94 from being removed or ejected from the trunnion 85.

A spring 104 or similar resilient structure is provided for urging the detent 94 toward the engaging position toward the first end 91 of the trunnion 85. The spring 104 is preferably formed as a coil disposed about the guide portion 98 of the detent 92, bearing against the second bearing portion 97 of the detent 92 and the closed end of the first bore 90.

When the detent 94 is positioned in the engaging position, the end of the first bearing portion 95 extends outwardly beyond the yoke arm 72 of the trigger arm 66. As will be further explained below, the user may push the face of the protruding first bearing portion 95 to move the detent 94 toward the disengaged position, compressing the spring 104. When the detent 94 is released, the spring 104 urges the detent 94 to move toward the engaged position thereof.

If desired, means for electrically energizing the actuating member 60 may be provided in order to use the instrument 10 for cauterization. Although the concept of using a laparoscopic surgical instrument for cauterization is conventional, the instrument 10 has a unique contact assembly 105 for energizing the actuating member 60 while permitting axial and rotary relative movement therebetween. As best seen in FIG. 6, the contact assembly 105 includes a socket 106 having a central bore 107 through which the actuating member 60 extends. The socket 106 is formed of a conductive solid material, preferably a copper alloy. A circumferential groove 108 is formed on the inner surface of the socket 106, within the bore 107.

A conventional canted coil spring 109 is retained in the groove 108, and provides a sliding conductive contact with the actuating member 60. The spring 109 may be formed from a beryllium-copper alloy and then silver plated. A suitable canted coil spring may be obtained from Bal Seal Engineering Company, Inc. of Santa Ana, Calif. In the canted coil spring 109, the coils are canted to one side about the circumference of the looped coil. This arrangement permits the actuating member 60 to be inserted through the bore 107 of the disk 105 with reduced effort to expand the spring 109, when compared to the effort required to insert the actuating member 60 past a coil spring in which the coils are not canted.

The socket 106 is provided with a set screw 110 which secures an electrical conductor 111 to the socket 106. As seen in FIG. 3, the conductor 111 is electrically connected to a plug 112 mounted to extend through the handle 11 of the instrument 10. Thus, electrical power for cauterization is supplied to the tool 13 through the plug 112, the conductor 110, the socket 106, the spring 104, and the actuating member 60. The patient is electrically grounded in a conventional manner to complete the electrical circuit required for cauterization.

The contact assembly 105 further includes a tubular socket housing 113 for supporting the socket 106. The socket housing 113 is fixed at the proximal end thereof to the distal face of the receiver portion 88 of the trunnion 85. The socket housing 113 holds the socket 106 with the bore 107 in the socket 106 in axial alignment with the second bore 93 through the trunnion 85. The socket 106 is captured in the socket housing 113 by a socket housing cap 114 fixed to the distal end of the socket housing 113. The socket housing cap 114 is disk-shaped and is formed with a central opening 115, through which the actuating member 60 extends into the socket 106. Preferably the distal end of the central opening 115 is chamfered or otherwise enlarged to ease the alignment and insertion of the actuating member 60 through the socket housing cap 114.

The socket housing 113 and the socket housing cap 114 are slidingly supported for reciprocation with the trunnion 85 within a tubular part of the receiver portion 15 of the handle 11. It should be noted that sufficient clearance must be provided between non-axially moveable components and the reciprocating trunnion 85 and contact assembly 105 to accommodate relative movement therebetween caused by movement of the trigger arm 66 between the actuated position and unactuated position.

The distal end of the receiver portion 15 of the handle 11 is formed into an opening 116, through which the actuating member 60 extends. A circumferential groove 117 is formed on the inner surface of the distal end of the receiver portion 115, spaced inwardly of the opening 116. The purpose of the groove 117 will be explained below.

Referring now to FIGS. 3 and 7, an adapter assembly 118 is provided for releasably securing the tube 61 of the shaft portion 12 to the handle 11. The adapter assembly 118 includes an adapter body 119. The adapter body 119 is formed with a central opening 120 to accommodate insertion of the shaft portion 12. The adapter body 119 is preferably formed with an annular extension 121 on the proximal end thereof. The extension 121 extends into the receiver portion 15 of the handle 11 through the opening 116. The extension 121 is formed with a radially outwardly extending flange 122 which engages the circumferential groove 117 in the receiver portion 15 of the handle 11 to retain the adapter body 119 on the distal end of the handle 11. Preferably the flange 122 fits tightly within the groove 117 so that adapter body 119 does not rotate freely relative to the handle 11, but rather will remain in a position to which the adapter body 119 is rotated by the user. The periphery of the adapter body 119 is preferably scalloped, as seen in FIG. 7, to enable the user to easily grasp and turn the adapter body 119.

The adapter body 119 is formed with a slot 123 extending linearly across the distal face thereof. Inwardly extending flanges 124 and 125 are formed on either side of the slot 123. An longitudinally extending groove 126 is formed in the radially outer surface of the adapter body 119 from the base of the slot 123 to the proximal face of the adapter body 119. A radially inwardly extending recess 127 is formed in the adapter body 119 spaced slightly apart longitudinally from the distal end of the groove 126. The purpose of the slot 123, the groove 126 and the recess 127 will be explained below. The adapter body is preferably molded of a suitable plastic material.

The adapter assembly 118 also includes an adapter detent 128. The adapter detent 128 is preferably a metallic part cast as a flat strip having a proximally-extending flange 129 formed at one end thereof. A generally pear-shaped opening 130 is formed through the adapter detent 128. The opening 130 has a wide portion 131, a receiver portion 132, and an elongated narrow portion 133. Preferably, the receiver portion 132 is beveled outwardly on the distal side thereof, for a purpose which will be discussed below.

The adapter detent 128 is reciprocally mounted in the slot 123. The flanges 124 and 125 extend over the adapter detent 128 to retain the adapter detent 128 in the slot 123. The flange 129 is disposed in the groove 126, and extends over the recess 127. A spring 134 is seated in the recess 127, and acts to urge the flange 129, and thus the adapter detent 128, radially outwardly. The detent is prevented from moving radially outwardly out of the slot 123 by a screw 135. The screw 135 extends through the narrow portion 133 of the opening 130 and is threaded into the adapter body 119.

When a user presses the flange 129 radially inwardly, compressing the spring 134, the wide portion 131 of the opening 130 in the adapter detent 128 is moved into alignment with the opening 115 in the socket housing cap 114. When the flange 129 is released, the spring 134 moves the adapter detent 128 radially outwardly until the adapter detent 128 is stopped by the screw 135. In this position, the receiver portion 132 of the opening 130 is in alignment with the opening 115 in the socket housing cap 114.

The shaft portion 12 has an adapter bushing 136 fixed about the proximal end of the tube 61. As best seen in FIG. 3, the bushing 136 generally increases in thickness toward the distal end thereof. A circumferential groove 137 is defined in the bushing 136 spaced from the distal end thereof. When the shaft 12 is installed in the handle 11, the adapter detent 128 is aligned with the groove 137 on the bushing 136.

The wide portion 131 of the pear-shaped opening 130 has a diameter which is slightly greater than the diameter of the adapter bushing 136 adjacent to the groove 137, but less than the diameter of the distal end of the adapter bushing 136. Thus, when the adapter detent 128 is positioned such that the wide portion 131 of pear-shaped opening 130 is aligned with the opening 115 in the socket housing cap 114, and thus centered about the adapter bushing 136, the adapter detent 128 is disengaged from the adapter bushing 136. When the adapter detent 128 is in this disengaged position, the adapter bushing 136 may be moved distally out of the adapter detent 128. However, when the groove 137 in the adapter bushing 136 is aligned with the adapter detent 128, the adapter detent 128 may be moved laterally relative to the adapter bushing 136, such that the receiver portion 96 of the adapter detent 128 engages the groove 137. When the adapter bushing 136 is thus engaged by the adapter detent 128, the position of the adapter bushing 136 is axially fixed relative to the adapter detent 128 and thus to the handle 11 to which the adapter assembly 118 is secured. The adapter detent 128 is thus in the engaged position.

As indicated above, the shaft portion 12 is releasably secured to the handle 11. To install the shaft portion 12, locking mechanism 78 is first released, to allow the trigger arm 66 to move distally to the first position thereof. Then, the detent 94 and the adapter detent 128 are moved to their disengaged positions. This may be easily accomplished by holding the handle in one hand such that the exposed first bearing portion 95 of the detent 94 is depressed with one finger while flange 129 of the adapter detent 128 is simultaneously depressed by the thumb of the same hand. The adapter assembly 118 may be rotated relative to the handle 11 to the most convenient position for operating the adapter detent 128. With the adapter detent 128 and the detent 94 held in their disengaged positions, the shaft portion 12 is inserted into the opening 130 through the adapter detent 128 with the user's other hand. The actuating member 60 is guided through the contact assembly 105, the trunnion 85, and into the insert 55 in the coupling 45. As indicated above, the distal end of the central opening 115 through the socket housing cap 114 is chamfered to ease the alignment and insertion of the actuating member 60 through the contact assembly 105. The coils of the spring 109 twist as they are pushed out of the way of the actuating member 60 as the actuating member 60 passes through the contact assembly 105. The spring 109 bears against the exterior of the actuating member 60 to provide an electrically conducting contact. As the actuating member 60 is inserted into the coupling 45, the tongue 63 engages the splines 56 on the interior of the insert 55, thus coupling the actuating member 60 for rotation with the motor assembly 29.

As the actuating member 60 is inserted into the handle 11, the adapter bushing 136 on the tube 61 is simultaneously inserted into the adapter assembly 118. The shaft portion 12 is inserted until the adapter bushing 136 bears against the distal face of the adapter body 119. The detent 94 can then be released to engage the groove 62 on the actuating member 60, and the adapter detent 128 released to engage the groove 137 on the adapter bushing 136. Thus the shaft portion 12 is installed on the handle 11 with the tube 61 axially fixed relative to the handle 11, and the actuating member 60 is connected to the operating mechanism 19 for reciprocation and rotation relative to the handle 11.

As indicated above, rotation of the actuating member 60 to rotate the tool 13 will normally cause the tool 13 to rotate the tube 61. This will cause the adapter bushing 136, which is fixed to the tube 61, to rotate relative to the adapter assembly 118 since the adapter body 119 does not rotate freely relative to the handle 11.

To release the shaft portion 12 from the handle 11, the detent 94 and the adapter detent 128 are each moved to their respective disengaged positions. The actuating member 60 and the tube 61 are thus quickly freed to permit removal of the shaft portion 12 from the handle 11.

Note that the unique attachment mechanism provided by the detent 94 and the adapter detent 128 permits rapid and simple removal and replacement of the shaft portion 12. This may be desired during the course of surgery, for example, to change from the gripping tool 13 to a scissors tool which would be supported on another shaft portion 12. In previously known instruments, removable shaft portions were secured to respective handles by means of a rotating locking ring, thumb screw, or threaded collar which first had to be rotated to release the shaft portion before the shaft portion could be grasped and removed from the handle.

In operation, a user selects the type of tool 13 which is to be used. For the sake of illustration, assume that the user wishes to perform suturing of an internal organ during laparoscopic surgery using a conventional suture needle with an attached ligature or suture. The tool 13 chosen by the user would be a gripper as illustrated in FIGS. 1 and 2. The user then installs the shaft portion 12 having the selected tool 13 onto the handle 11, as described above. Grasping the grip portion 14 of the handle 11 with one hand, the user can use fingers of the same hand to move the trigger arm 66 toward the grip portion 14 and thereby actuate the tool 13 to grasp the suture needle (not shown). The user then actuates the locking mechanism 78 by pressing on the arm 84*a* of the bell crank lever 84, thus locking the trigger arm 66 in place. This allows the user to release the trigger arm 66 without dropping the suture needle. It will be understood that, as pointed out above, the locking mechanism 78 is capable of securing the position of the trigger arm 66 relative to the handle 11 at any point in the travel of the trigger arm 66. This advantageously permits the instrument 10 to be locked grasping any item within the range capable of being grasped by the tool 13, not merely relatively small objects like a needle.

The instrument 10 is then positioned for use by inserting the tool 13 and shaft portion 12 through a laparoscopic guide tube (not shown) installed through a patient's abdominal wall. By manipulating the instrument 10, the user can pass the needle partially through the tissue to be sutured. While gripping the finger grip 70 of the trigger arm 66 with one or two fingers, the user presses on the arm 84*b* of the lever 84 with another finger, causing the locking mechanism 78 to move the pawl 80 out of engagement with the ratchet 79, and release the trigger arm 66. Since the user was gripping the trigger arm 66, the user can control the rate at which the spring 77 moves the trigger arm back to the first position thereof, causing the tool 13 to release the needle. The tool 13 can then be closed on the protruding portion of the needle to pull it the rest of the way through the tissue, thus pulling the suture fixed to the needle through the tissue. The suture is cut between the tissue and the needle, leaving first and second ends of the suture (not shown) extending from the tissue. The user grasps the first end of the suture in the tool 13. The user depresses a thumb switch 27 or 28 to cause the tool 13 and the tube 61 to rotate three revolutions in a first direction. As discussed above, the microprocessor of the control circuit 25 can be programmed to cause, for example, a full rotation for a single momentary depression of a thumb switch 27 or 28. Simultaneously the user manipulates a second instrument (not shown), which may be a conventional gripper tool, to guide the portion of material between the tissue and the first end of the suture proximally, thus causing the suture to form three wraps around the tube 61. The first end of the suture is then grasped by the second instrument, and the tool 13 operated to release the first end of the suture. The tool 13 is then moved to grasp the second end of the suture, while maintaining the wraps around the tube 61. The instrument 10 and the second instrument are then pulled relatively away from each other, causing the wraps to slide off the tube 61 and down around the second end of the suture. Carefully releasing the first end of the suture so that the wraps remain around the second end of the suture, the user grasps the second end of the suture with the second instrument. Then the user manipulates the instrument 10 to release the second end of the suture and grasp the first end of the suture with the tool 13. The user actuates a thumb switch 27 or 28 to cause the tool 13 rotate in the opposite direction from the first direction, causing a single wrap to form about the tube 61. After exchanging grips once again, without allowing the wrap to slide off the tube 61, the user grasps the second end of the suture in the tool 13, and the first end of the suture with the second instrument. The instruments are then pulled apart again to form a slip knot of a type conventionally used in surgery for securely suturing tissue.

Figure 8:
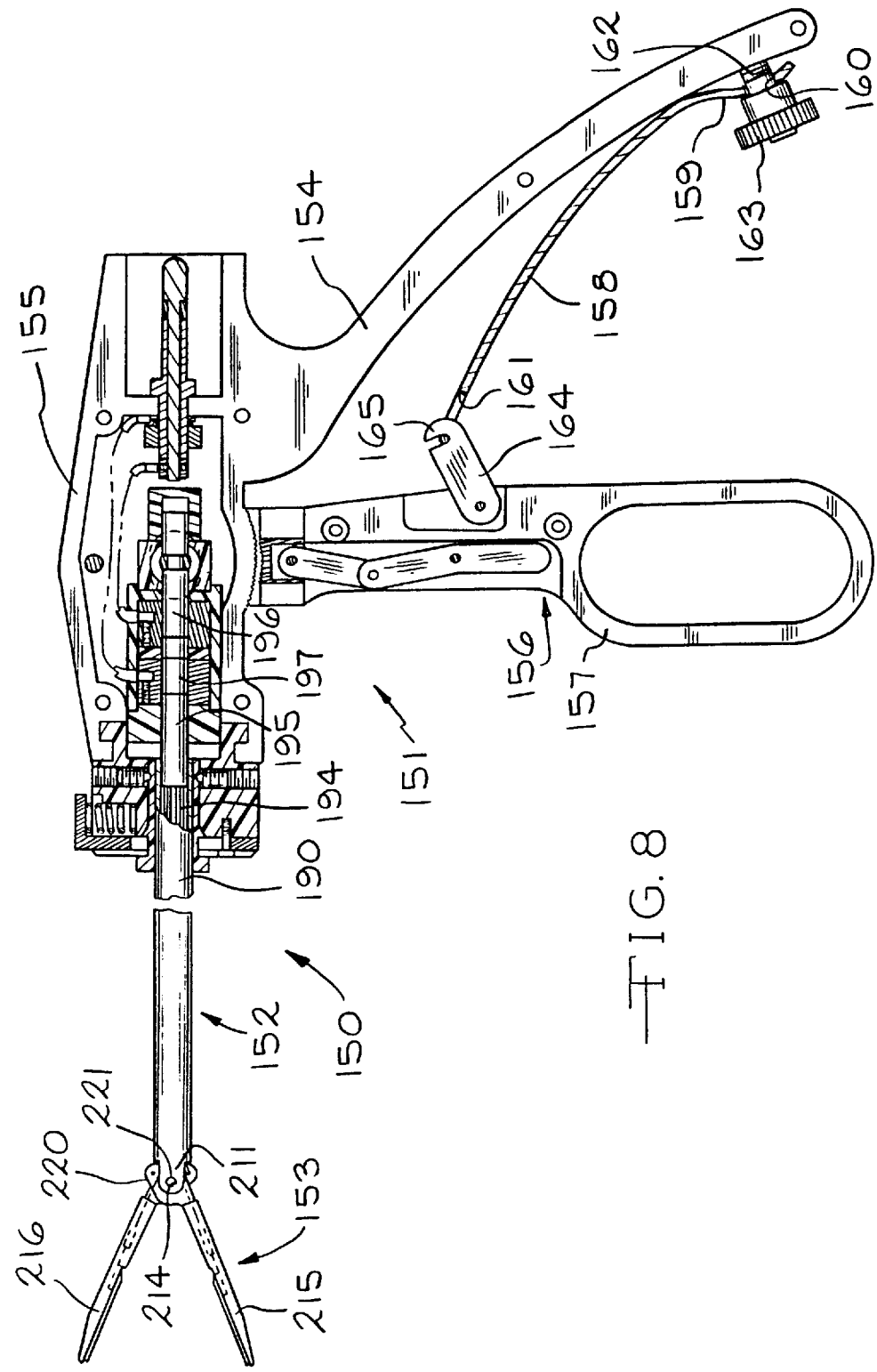
FIG. 8 is a fragmentary elevational view, partly in section, of a second embodiment of a laparoscopic surgical instrument in accordance with this invention.

Referring now to FIG. 8, a second embodiment of a laparoscopic surgical instrument, indicated generally at 150, in accordance with this invention is shown. The instrument 150 includes a pistol-shaped handle 151, a shaft portion 152 releasably fixed to the distal end of the handle 151, and a tool 153 mounted on the distal end of the shaft portion 152.

The handle 151 is preferably constructed of two symmetrical side pieces to form a grip portion 154 and a hollow receiver portion 155, in a manner similar to the handle 11 described above. The handle 151 includes an actuating structure 156, which is structurally similar to the actuating structure 65 described above. The actuating structure 156 includes a trigger arm 157 pivotally mounted on the receiver portion 155 of the handle 151 for movement relative thereto.

A spring 158 or other resilient structure is provided for urging the trigger arm 157 to a first position, relatively away from the grip portion 154 of the handle 151. The first position of the trigger arm 157 corresponds to the unactuated condition of the tool 153. As with the first embodiment described above, when the trigger arm 157 is moved toward the handle 151 to a second position relatively closer to the grip portion 154, the tool 153 is actuated. The trigger arm 157 is provided with a releasable locking mechanism, identical in structure and operation to the locking mechanism 78 described above, for selectively retaining the trigger arm 157 in a selected position relative to the grip portion 154.

The spring 158 is preferably a leaf spring formed from a curved metallic strap, generally formed as a continuous arc, but having an S-shaped curve 159 near the proximal end thereof. A first opening 160 is formed through the spring 158, spaced slightly from the proximal end thereof. A second opening 161 is formed through the spring 158 near the distal end thereof. A threaded stud 162, which is fixed to the lower end of the grip portion 154 extends through the first opening 161 in the spring 158. A thumbnut 163 is threaded onto the stud 162 to secure the spring 158 to the grip portion 153. Tightening the thumbnut 163 will urge the spring 158 to pivot about a portion of the S-shaped curve 159, urging the trigger arm 157 away from the grip portion 154 of the handle 151. Thus, tightening the thumbnut 163 increases the tension in the spring 158. Conversely, loosening the thumbnut 163 decreases the tension in the spring 158, thus making it easier for a user to move the trigger arm 157 toward the grip portion 154 of the handle 151. In this manner, operation of the thumbnut 163 permits the user to select a desired amount of tension in the spring 158.

The spring 158 is coupled to the trigger arm 157 by a link 164. The link 164 is pivotally mounted at a first end thereof in a recess formed on the proximal side of the trigger arm 157. A hook 165 is formed on a second end of the link 164 which engages the opening 161 in the distal end of the spring 158 to couple the link 164 and the spring 158. The spring 158 exerts a force axially through the link 164 to urge the trigger arm 164 away from the grip portion 154 of the handle 151 as described above. As the trigger arm 157 is moved relative to the grip portion 154 of the handle 151, the link 164 pivots to accommodate the resultant relative motion between the distal end of the spring 158 and the trigger arm 164.

Referring now to FIG. 9, the receiver portion 155 of the handle 151 has a pair of opposed oval openings 166 (one of which is shown by a broken line) formed through the side pieces thereof. A trunnion 167, identical in structure and function to the trunnion 85 described above, extends through the openings 166 in the receiver portion 155, between the yoke arms of the trigger arm 157. Thus, the trigger arm 157 may be moved to move the trunnion 167 axially within the receiver portion 155.

A bore 168 extends through the trunnion 167 coaxially with the receiver portion 155. A cap 169 is fixed to the proximal face of the trunnion 167, sealing the proximal end of the bore 168. A detent 170 is reciprocal within the trunnion 167. The detent 170 has a pear-shaped opening 171 therethrough for releasably engaging the shaft portion 152 as will be further described below.

A contact assembly 172, generally similar to the contact assembly 105 described above, includes a generally cylindrical socket housing 173 fixed to the distal face of the trunnion 167 for movement therewith. A proximal socket 174 and a distal socket 175, each of which are identical in structure to the socket 106 described above, are supported within the socket housing 173. A canted coil spring 176, or other suitable means for providing a sliding conductive contact with the shaft portion 152, is captured within a circumferential groove within the bore formed through each of the sockets 174 and 175. An electrically insulating washer 177 is interposed between the sockets 174 and 175. An annular socket housing cap 178 is secured to the distal end of the socket housing 173 to capture the sockets 174 and 175 within the socket housing 173. The central openings of the sockets 174 and 175, the insulating washer 177, and the socket housing cap 178 are coaxially aligned with the bore 168 through the trunnion 167.

The sockets 174 and 175 may be electrically energized via respective conductors 179 from a conventional bipolar plug 180 extending through the proximal end wall of the receiver portion 155 of the handle 151. As in the first embodiment, the conductors 179 must be sufficiently long and flexible to accommodate the relative movement between the plug 180 and the contact assembly 172. The handle 151 preferably includes a molded annular guard 181 about the outwardly projecting portion of the plug 180.

An adapter assembly 182, similar in structure and function to the adapter assembly 118 described above is rotatably mounted on the distal end of the receiver portion 155. The adapter assembly 182 includes a body 183 having an axial bore 184 therethrough. An adapter detent 185 having a pear-shaped opening 186 therethrough is reciprocally mounted on the body 183. As will be further discussed below, the body 183 is preferably provided with axially-extending grooves 187 to facilitate a user's rotation of the body 183 relative to the receiver portion 155 of the handle 151.

Unlike the adapter assembly 118, the adapter assembly 182 includes a pair of opposed conventional ball plungers 188. Each ball plunger 188 is mounted by means of external threads thereon in a respective threaded bore 189 extending radially from exterior of the body 183 to the axial bore 184 through the body 183 of the adapter assembly 182. The spring-loaded balls of each ball plunger 188 extends at least partially into the axial bore 184 of the body 183, for a purpose which will be explained below.

As illustrated in FIGS. 8 through 10, the shaft portion 152 of the instrument 150 is generally similar to the shaft portion 12 described above. The shaft portion 152 includes an outer tube 190. The interior surface of the distal end of the tube 190 is threaded for mounting the tool 153. An adapter bushing 191 is fixed about the proximal end of the tube 190. The adapter bushing 191 has a structure which is similar to the adapter bushing 136 described above, being tapered inwardly toward the proximal end thereof, and having a circumferential groove 192 formed near the distal end thereof. A plurality of opposed pairs of semi-spherical recesses 193 are spaced about the circumference of the adapter bushing 136 intermediate the groove 192 and the proximal end of the adapter bushing 136, the purpose of which will be explained below.

The shaft portion 152 also includes an actuating member 194 which is axially reciprocal within the tube 190. The proximal end of the actuating member 194 is fixed to a cylindrical connector body 195, preferably by molding the connector body 195 around the distal end of the actuating member 194. The distal end of the actuating member 194 may be knurled or otherwise shaped to improve resistance to being pulled out of the connector body 195.

The connector body 195 is provided with a pair of electrical contacts 196 and 197, each made of a suitable electrically conductive material. The contact 196 is generally cylindrical, and has a circumferential groove 198 formed about a portion thereof. A reduced diameter distal portion 199 of the contact 196 extends into the proximal end of the connector body 195. An electrical conductor 200 is electrically connected, for example by soldering, to the distal portion 199 of the contact 196.

The contact 197 is generally tubular and is disposed about the distal portion 199 of the contact 196. The contact 197 is swaged or otherwise formed to reduce the diameter of a distal portion 201 of the contact 197. The inner diameter of the distal portion 201 of the contact 197 is greater than the outer diameter of the distal portion 199 of the contact 196, so that the contact 197 is spaced apart from the contact 196. The distal portion 201 of the contact 197 is electrically connected to an electrical conductor 202.

The contacts 196 and 197 are held in fixed relationship relative to the actuating member 194 by the connector body 195. The connector body 195 is preferably formed by insert molding an insulating plastic material over the distal portions of the contacts 196 and 197, and over the proximal ends of the conductors 200 and 202, along with the proximal end of the actuating member 194 as described above. Thus the proximal ends of the contacts 196 and 197 are left exposed, the purpose of which will be described below.

Referring now to FIG. 10, the distal end of the actuating member 194 is fixed to a cylindrical connector body 203, preferably by insert molding the connector body 203 around the distal end of the actuating member 194. The distal end of the actuating member 194 may be knurled or otherwise shaped to improve resistance to being pulled out of the connector body 203. The conductors 200 and 202 extend through the connector body 203.

A pair of spaced apart connecting members 204 and 205 extend axially from the distal end of the connector body 203. The connecting members 204 and 205 are fixed to the connector body 203, preferably by insert molding the connector body 203 about the respective proximal ends of the connecting members 204 and 205. The connecting members 204 and 205 may advantageously be formed from a single U-shaped length of spring wire, the bight (not shown) of which is encased in the connector body 203. The distal end of each of the connecting members 204 and 205 is formed into a respective inwardly extending arm 206 and 207. The connecting members 204 and 205 are bent radially outwardly in opposite directions so that the arms 206 and 207 are transversely offset from one another. The purpose of the arms 206 and 207 will be explained below.

As is best seen in FIG. 10, the tool 153 includes a generally tubular body 210. The body 210 is provided with threads on the outer surface of the proximal end thereof which engage the threads formed on the interior surface of the outer tube 190 of the shaft portion 152 to fix the body 210 on the distal end of the shaft portion 152. The body 210 has a pair of axially extending yoke arms 211 (FIG. 8) and 212 (shown in broken line in FIG. 10). A respective pivot hole 214 is formed through each of the yoke arms 211 and 212, the purpose of which will be explained below.

The tool 153 her includes a pair of jaws 215 and 216 which are mutually relatively moveable. The jaw 215 includes an elongate gripping portion 217. A metallic contact 218 is fixed to the gripping portion 217. Preferably, the contact 218 is formed by stamping, although other forms of forming the contact 218, such as wire forming are also contemplated. The electrical conductor 202 is electrically connected, for example by soldering, to the contact 218. The gripping portion 217 is preferably formed of an electrically insulating, rigid plastic material which is molded about portions of the contact 218 and the distal portion of the conductor 202 to fix the contact 218 to the gripping portion 217 for a purpose which will be discussed below. A flange 220 is formed on the proximal end of the gripping portion 217, preferably being integrally molded with the gripping portion 217. A pivot pin 221 extends perpendicularly from the flange 220 into the pivot hole 214 (FIG. 8) of the yoke arm 211 adjacent to the jaw 215, the purpose of which will be explained below. An opening 222 is formed through the proximal end of the flange 220, and is engaged by the arm 206 formed on the connecting member 204. The jaw 215 is thus connected to the connector body 203 for actuation thereby. A connector pin 224 extends from the flange 220 opposite the pin 221 to engage a mating recess 225 in a flange 223 formed on the jaw 216 with a snap fit, thereby allowing the jaws 215 and 216 to be coupled together and pivoted relative to one another.

Except for the recess 225 described above, the jaw 216 is otherwise constructed similarly to the jaw 215, having a gripping portion 226 formed on the distal end of the flange portion 223. The gripping portion 226 is provided with an exposed contact 227 which is electrically connected to the conductor 200. Note that since the gripping portions 217 and 226 are formed of an electrically insulating material, no current path is provided between the conductors 202 and 200 through the jaws 215 and 216. A second pivot pin (not shown), similar to the pivot pin 221, extends outwardly from the flange portion 223 to engage the pivot hole 214 of the yoke arm 212. The second pivot pin and the pivot pin 221 are coaxially aligned with the connector pin 224 and cooperate with the pivot holes 214 in the respective adjacent yoke arms 212 and 211 to pivotally mount the coupled jaws 215 and 216 to the body 210 of the tool 153. An opening 228 is formed through the proximal end of the flange portion 223, which is engaged by the arm 207 on the connecting member 205. The jaw 216 is thereby connected to the connector body 203 for actuation thereby.

The procedure for connecting the shaft portion 152 to the handle 151 is generally the same as that for connecting the shaft 12 to the handle 11 of the first embodiment, as described above. The locking mechanism is first released, to allow the trigger arm 157 to move distally to the first position thereof. Then the detent 170 and the adapter detent 185 are moved to their disengaged positions. The adapter assembly 182 may be rotated relative to the handle 151 to the most convenient position for operating the adapter detent 185. With the adapter detent 185 and the detent 170 held in their disengaged positions, the shaft portion 152 is inserted into the opening 186 through the adapter detent 185 with the user's other hand. The actuating member 194 is guided through the contact assembly 172, the trunnion 167, and into the cap 169. The spring 176 in the socket 174 bears against the electrical contact 196 provide an electrically conducting contact therebetween. Similarly, the spring 176 in the socket 175 bears against the electrical contact 197 to provide an electrically conducting contact therebetween.

As the actuating member 194 is inserted into the handle 151, the adapter bushing 191 on the outer tube 190 is simultaneously inserted into the adapter assembly 182. The shaft portion 152 is inserted until the adapter bushing 191 bears against the distal face of the adapter body 183. The detent 170 can then be released to engage the groove 198 on the actuating member 194, and the adapter detent 185 released to engage the groove 192 on the adapter bushing 191. It may be necessary to move the trigger arm 157 slightly to permit the detent 170 to engage the groove 198 on the actuating member 194. The shaft portion 152 is thus installed on the handle 151 with the outer tube 190 axially fixed relative to the handle 151, and the actuating member 194 is connected to the actuating structure 156 for reciprocation with the trigger arm 157.

Additionally, the balls of the ball plungers 188 are axially aligned to engage the recesses 193 on the adapter bushing 191. The recesses 193 may be engaged by the ball plungers 188 immediately upon insertion of the shaft portion 152 into the handle 151. However, it may be necessary to rotate the outer tube 190 and the attached adapter bushing 191 relative to the handle 151 to radially align a pair of the recesses 193 with the ball plungers 188. Once the ball plungers 188 are axially and radially aligned with a pair of the recesses 193, the balls of the ball plungers 188 will engage respective ones of the recesses 193. The adapter bushing 191 and the outer tube 190 are thereby releasably fixed to the adapter assembly 182 for rotation therewith.

In operation, a user (not shown) will grasp the instrument 150 by the handle 151 with one hand. To rotate the tool 153 to a desired orientation relative to the handle 151, the user grasps and rotates the body 183 of the adapter assembly 182. The grooves 187 provide a relatively slip-resistant surface for grasping the body 183. The ball plungers 188 couple the body 183 to the adapter bushing 191 such that when the body 183 is rotated, the adapter bushing 191 and the outer tube 190 also rotate. The tool 153 is fixed to the outer tube 190 and thus rotates therewith.

To actuate the tool 153, the user moves the trigger arm 157 from the first position thereof proximally to a second position relatively closer to the grip portion 154 of the handle 151. The trunnion 167 consequently moves the actuating member 194 proximally within the handle 151, causing the connector body 203 to move proximally relative to the outer tube 190. This in turn causes the connecting members 204 and 205 attached to the connector body 203 to draw the openings 222 and 228 relatively closer together, and the gripping portions 217 and 226 to move toward one another. Releasing the trigger arm 157 permits the spring 158 to drive the trigger arm 157 back toward the first position thereof, resulting in the connector body 203 moving relatively toward the tool 153. This causes the connecting members 204 and 205 to drive the proximal end of flanges 220 and 223 relatively apart and also causes the gripping portions 217 and 226 to move relatively apart.

As indicated above, the contacts 218 and 227 are electrically isolated from one another by the respective gripping portions 217 and 226 which are made of an electrically insulating material. A conventional electrosurgical generator having a bipolar electrical potential output may be connected to the instrument 150 via the plug 180. A user may then actuate the tool 153 to grasp selected tissue between the jaws 215 and 216. The user can then actuate the generator to apply an electrical potential between the contacts 218 and 227, thereby causing electrical current to flow through the tissue interposed between the contacts 218 and 227. This may be desired, for example, to cauterize a wound during surgery.

Figure 12:
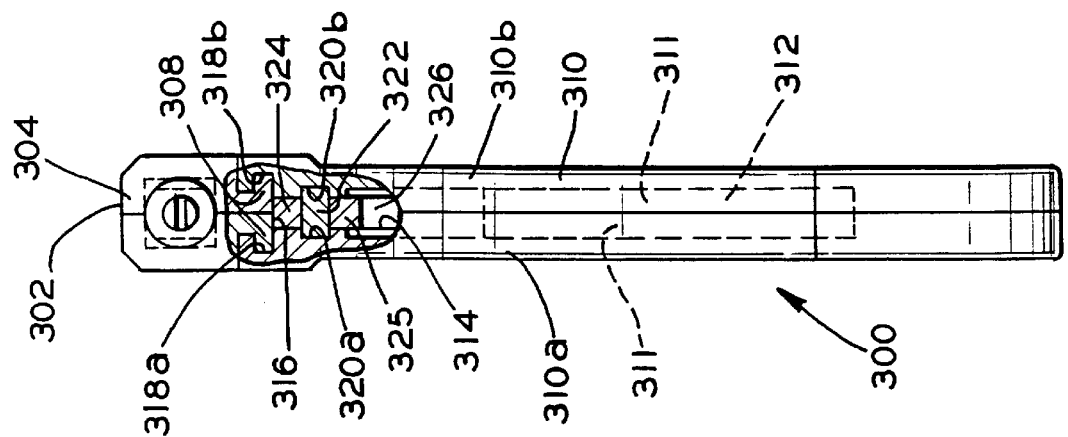
FIG. 12 is a proximal end view, partly in section, of the instrument shown in FIG. 11.
Figure 11:
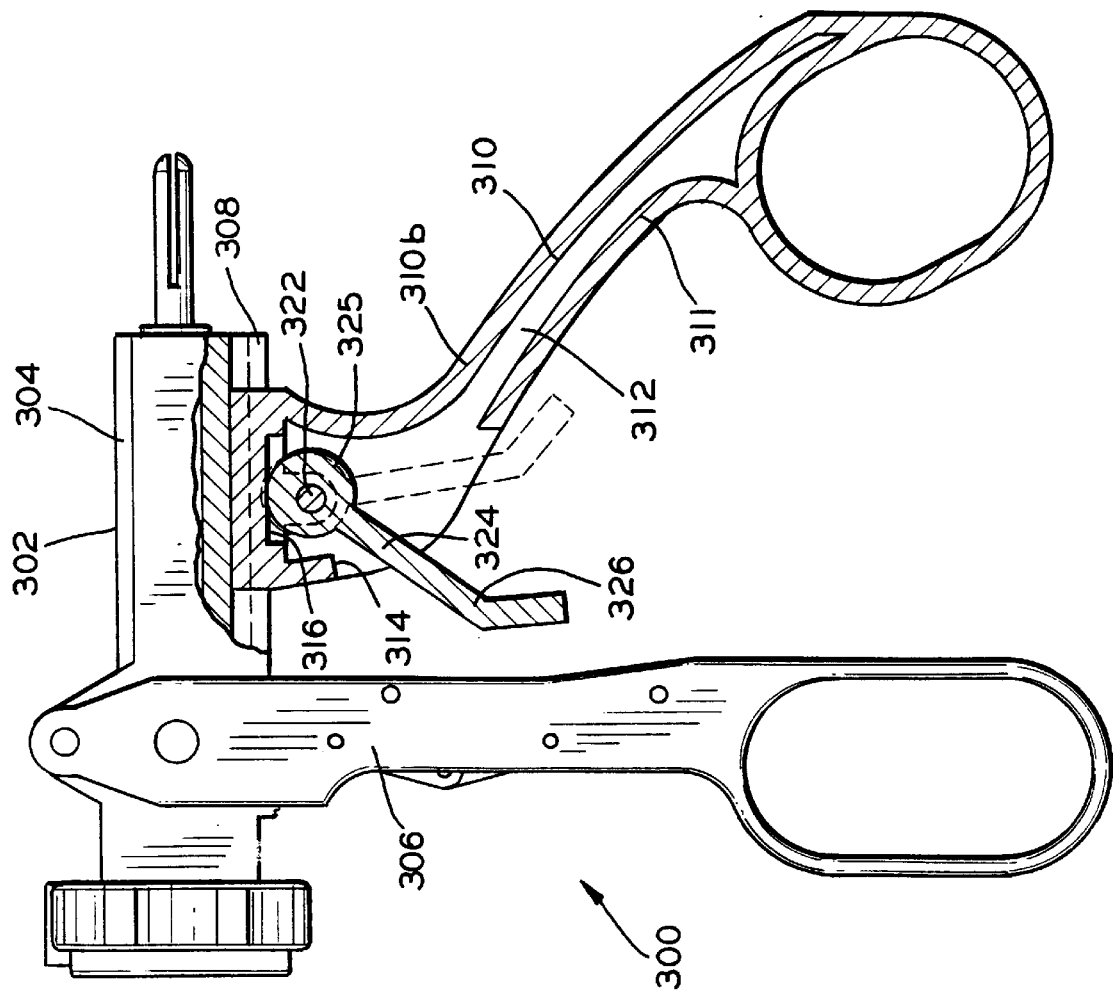
FIG. 11 is an elevational view, partly in section, of a third embodiment of a laparoscopic surgical instrument in accordance with this invention, and having an adjustably mounted grip portion.

Referring now to FIGS. 11 and 12, a third embodiment of a laparoscopic surgical instrument in accordance with this invention is shown generally at 300. The instrument 300 includes a pistol-shaped handle 302, which is preferably constructed of two symmetrical side pieces to form a hollow receiver portion 304, in a manner similar to the handles 11 and 151 described above. The handle 302 includes an actuating structure having a trigger arm 306 pivotally mounted on the receiver portion 304 of the handle 302 for movement relative thereto.

The proximal end of the receiver portion 304 is provided with an elongated flange 308 defining a longitudinal axis of the receiver portion 304. The flange 308 has a T-shaped cross section for adjustably mounting a grip portion 310 on the receiver portion 304. As shown in FIG. 12, each half of the receiver portion 304 preferably forms one half of the flange 308.

The grip portion 310 is preferably constructed of two symmetrical side pieces, 310a and 310b. Each of the side pieces 310a and 310b is provided with a respective flange 311 which extends about most of the periphery of the respective side piece 310a or 310b, and which extends toward the other of the side pieces 310a and 310b. The flanges 311 on the side pieces 310a and 310b cooperate with the side pieces 310a and 310b to generally define a hollow interior space 312 within the grip portion 310. A discontinuity in the flanges 311 forms a first opening 314 into the grip portion 310. A second opening 316 into the grip portion 310 exposes the T-shaped flange 308 of the receiver portion 304 to the interior space 312 of the grip portion 310, for a purpose which will be discussed below.

Each of the side pieces 310a and 310b is provided with a respective longitudinally extending recess, 318a and 318b. The recesses 318a and 318b cooperate to define a T-shaped slot which receives the flange 308 to mount the grip portion 310 for sliding movement relative to the receiver portion 304 along the longitudinal axis defined by the flange 308. Each of the side pieces 310a and 310b is also provided with a respective cylindrical recess, 320a and 320b. The recesses 320a and 320b cooperate to mount a pin 322 therein.

A locking, mechanism is provided for selectively fixing the relative positions of the grip portion 310 and the receiver portion 304. The locking mechanism includes a locking cam 324. The cam 324 has a disc-shaped body 325 and a depending arm 326, which is eccentrically mounted on the pin 322. The arm 326 extends out of the interior space 312 of the grip portion 310 through the opening 314, where it may be easily manipulated by a user of the surgical instrument 300. In a first position, illustrated in solid line in FIG. 11, the body 325 of the cam 324 is spaced apart from the flange 308, and the grip portion 310 is free to move longitudinally relative to the receiver portion 304 of the handle 302. In this manner, a user of the surgical instrument 300 may adjust the distance between the trigger arm 306 and the grip portion 310 as needed to provide a comfortable grip. Once a position is found which is comfortably fits the size of the user's hand, the arm 326 of the cam 324 is operated to move the cam 324 to the lock position illustrated in dashed line in FIG. 11. As the cam 324 is rotated into the lock position, the eccentrically mounted body 325 is urged through the opening 316 into contact with the flange 308. The cam 324 is wedged against the flange 308 in the lock position, fixing the position of the grip portion 310 on the receiver portion 304.

Figure 14:
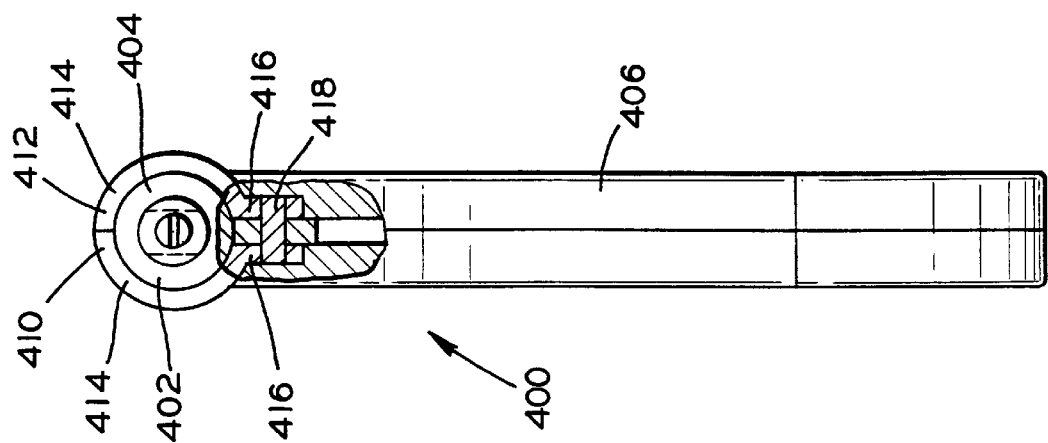
FIG. 14 is a proximal end view, partly in section, of the instrument shown in FIG. 13.
Figure 13:
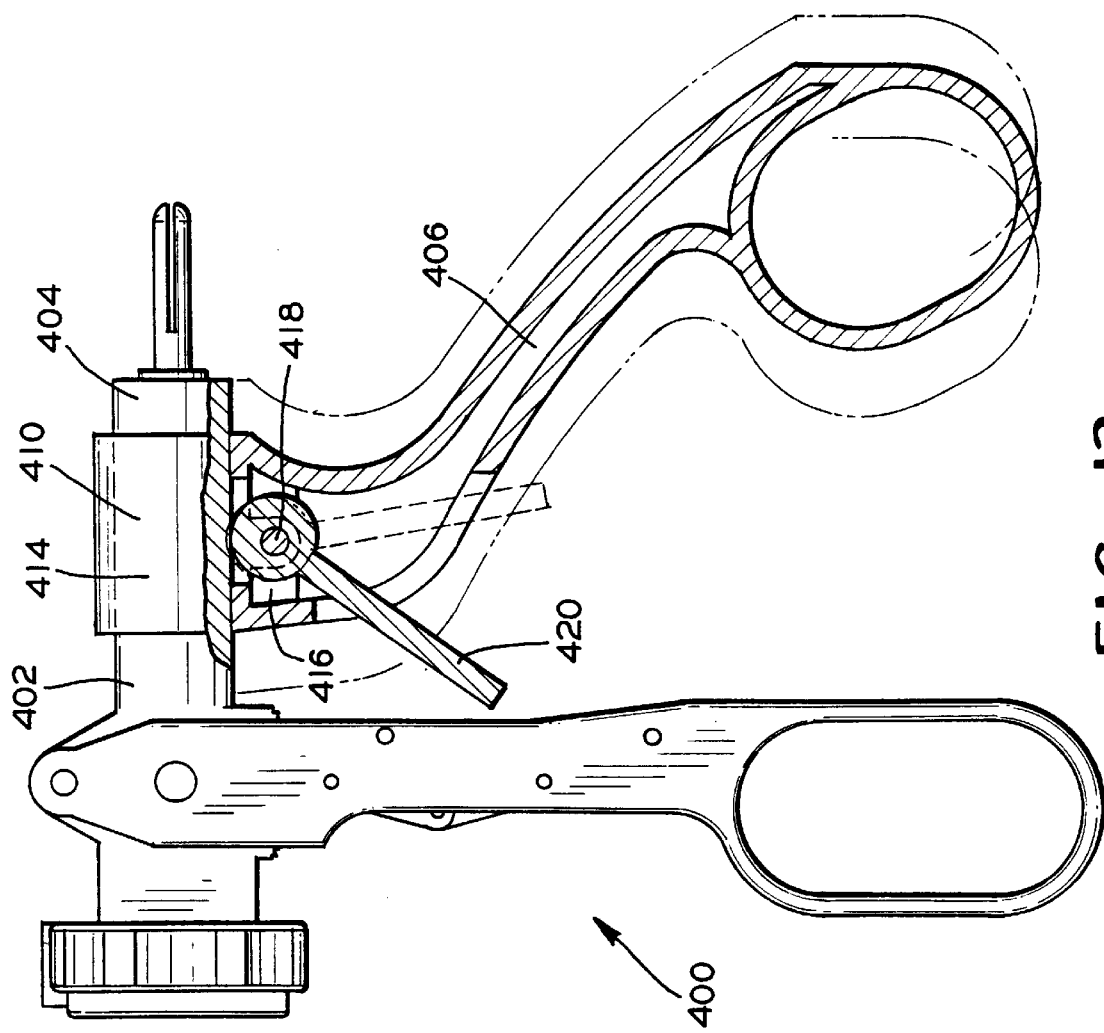
FIG. 13 is a view similar to FIG. 11 showing a fourth embodiment of the instrument of this invention, showing a different structure for adjustably mounting the grip portion of the handle portion.

FIGS. 13 and 14 illustrate a fourth embodiment of a laparoscopic surgical instrument, indicated generally at 400, in accordance with this invention. The instrument 400 includes a pistol-shaped handle 402, which is generally similar to the handle 302 described above. The handle 402 includes a receiver portion 404 having a proximal end which is generally cylindrical. The handle 402 also includes a grip portion 406 which is adjustably mounted on the receiver portion 404.

Unlike the grip portion 310, the grip portion 406 is provided with a pair of clamp members 410 and 412. Each of the clamp members 410 and 412 has a respective curved wall 414, and a respective ear 416 extending from one longitudinally extending edge of the respective curved wall 414. The curved walls 414 of the clamp members 410 and 412 cooperate to substantially encircle the proximal end of the receiver portion 404. The flat plates 416 of the clamp members 410 and 412 are parallel and spaced apart from one another. Each of the flat plates 416 has an aperture formed therethrough. A pin 418 is fixed in the apertures formed in the flat plates 416 of the clamp members 410 and 412, extending between the flat plates 416. The flat plates 416 of the clamp members 410 and 412 are fixed to respective halves of the grip portion 406 by any suitable means. Note that although the grip portion 406 is preferably formed from two symmetric mating pieces, the grip portion 406 of the laparoscopic surgical instrument 400, as in the other embodiments of the laparoscopic surgical instrument of this invention, may be suitably formed as a unitary part, or formed from any suitable number of parts. Also, the clamp members 410 and 412 may be formed as a single piece, or may be formed as integral parts of respective ones of the two halves of the grip portion 406.

A locking mechanism is provided, which includes a locking cam 420. The locking cam 420, similar to the cam 324 described above, is eccentrically mounted on the pin 418. While holding the laparoscopic surgical instrument 400, the user may use his or her fingers to easily move the cam 420 from an unlock position (shown in solid line in FIG. 13) to a lock position (shown in dashed lines in FIG. 13). In the unlock position, the cam 420 is disengaged from the receiver portion 404, and the grip portion 406 may be moved relative to the receiver portion 404. If desired, the grip portion 406 may be rotated relative to the receiver portion 404, as well as being moved longitudinally relative thereto as depicted by the phantom lines of FIG. 13. When the cam 420 is moved to the lock position, the cam 420 moves into engagement with the proximal end of the receiver portion 404, and is wedged between the pin 418 and the receiver portion 404 to fix the position of the grip portion 406 on the receiver portion 404.

Figure 17:
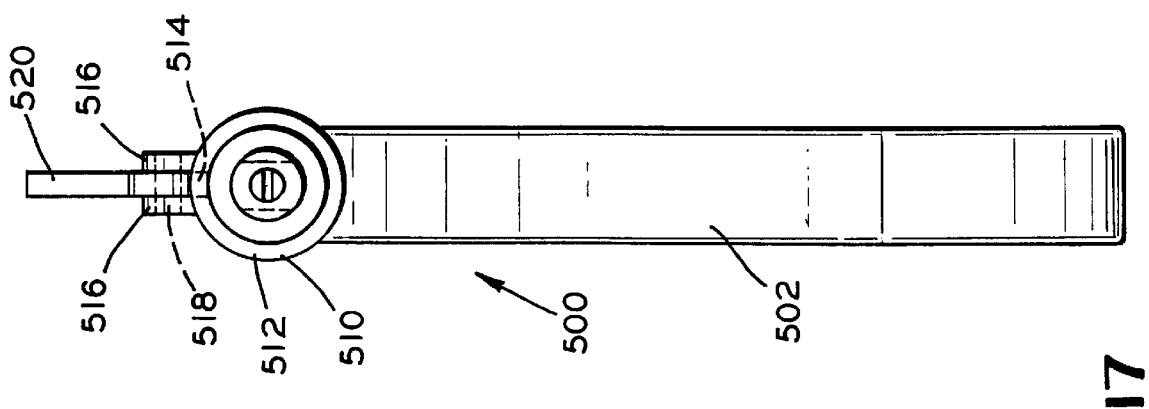
FIG. 17 is a proximal end view, partly in section, of the instrument shown in FIGS. 15 and 16.
Figure 16:
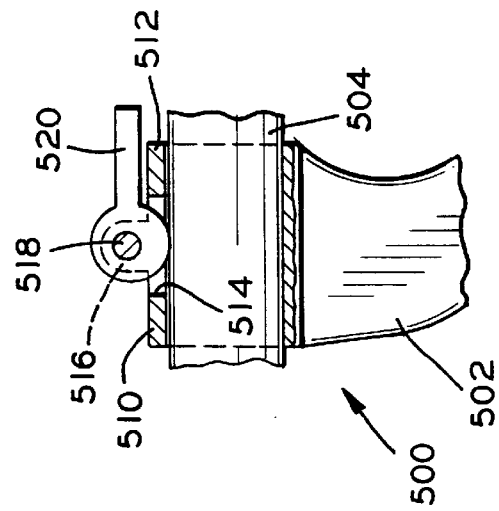
FIG. 16 is a view similar to FIG. 15, showing the cam of the locking mechanism thereof in a lock position.
Figure 15:
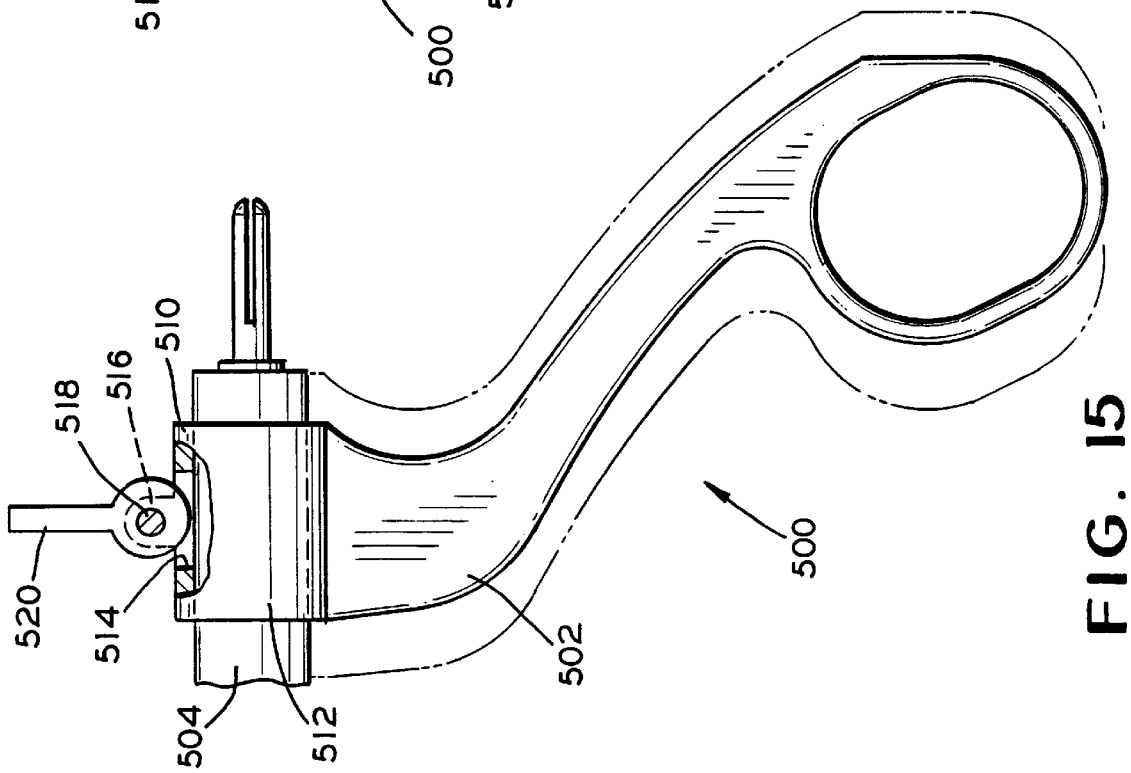
FIG. 15 is fragmentary view, partly in section, showing a fifth embodiment of the instrument of this invention, showing a different structure for adjustably mounting the grip portion of the handle portion.

FIGS. 15 through 17 illustrate a fifth embodiment of a laparoscopic surgical instrument in accordance with this invention, which is indicated generally at 500. The instrument 500 is generally similar to the instrument 400 described above, and has a grip portion 502 adjustably mounted on the cylindrical proximal end of a receiver portion 504. The grip portion 502 is fixed to, or integrally formed with a clamp member 510. The clamp member 510 includes a tubular body 512 encircling the proximal end of the receiver portion 504. A longitudinally extending opening 514 is formed through the body 512 opposite to the grip portion 502. Adjacent each longitudinally extending edge of the opening 514 is a respective outwardly extending ear 516. The ears 516 are parallel to each other, and are spaced apart from one another by the transverse width of the opening 514. A pin 518 is mounted transversely on the clamp 510, extending between the ears 516. A locking mechanism is provided, which includes a locking cam 520. The locking cam 520 is eccentrically mounted on the pin 518. The locking cam 520 is similar in function to the locking cam 420 described above, but mounted on the opposite side of the receiver portion 504 from the grip portion 502 of the instrument 500.

The locking cam 520 is shown in an unlock position in FIG. 15. In the unlock position, the cam 520 is disengaged from the receiver portion 504, and the grip portion 502 may be moved relative to the receiver portion 504. If desired, the grip portion 502 may be rotated relative to the receiver portion 504, as well as being moved longitudinally relative thereto as depicted by the phantom lines of FIG. 15.

When the cam 520 is moved to the lock position, illustrated in FIG. 15, the cam 520, extending into the opening 514, moves into engagement with the proximal end of the receiver portion 504. The cam 520 is wedged between the pin 518 and the receiver portion 504 to fix the position of the grip portion 502 on the receiver portion 504. The instrument 500 may thus be seen to be very similar in structure and function to the instrument 400, but having the locking cam 520 mounted to engage the upper surface (as seen in FIGS. 15 through 17) of the receiver portion 504 rather than the lower surface thereof.

Figure 19:
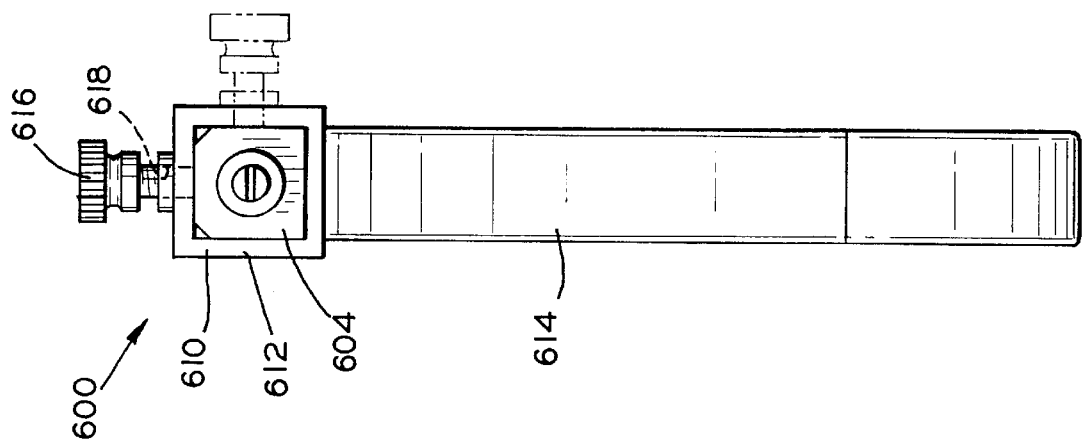
FIG. 19 is a proximal end view of the instrument shown in FIG. 18.
Figure 18:
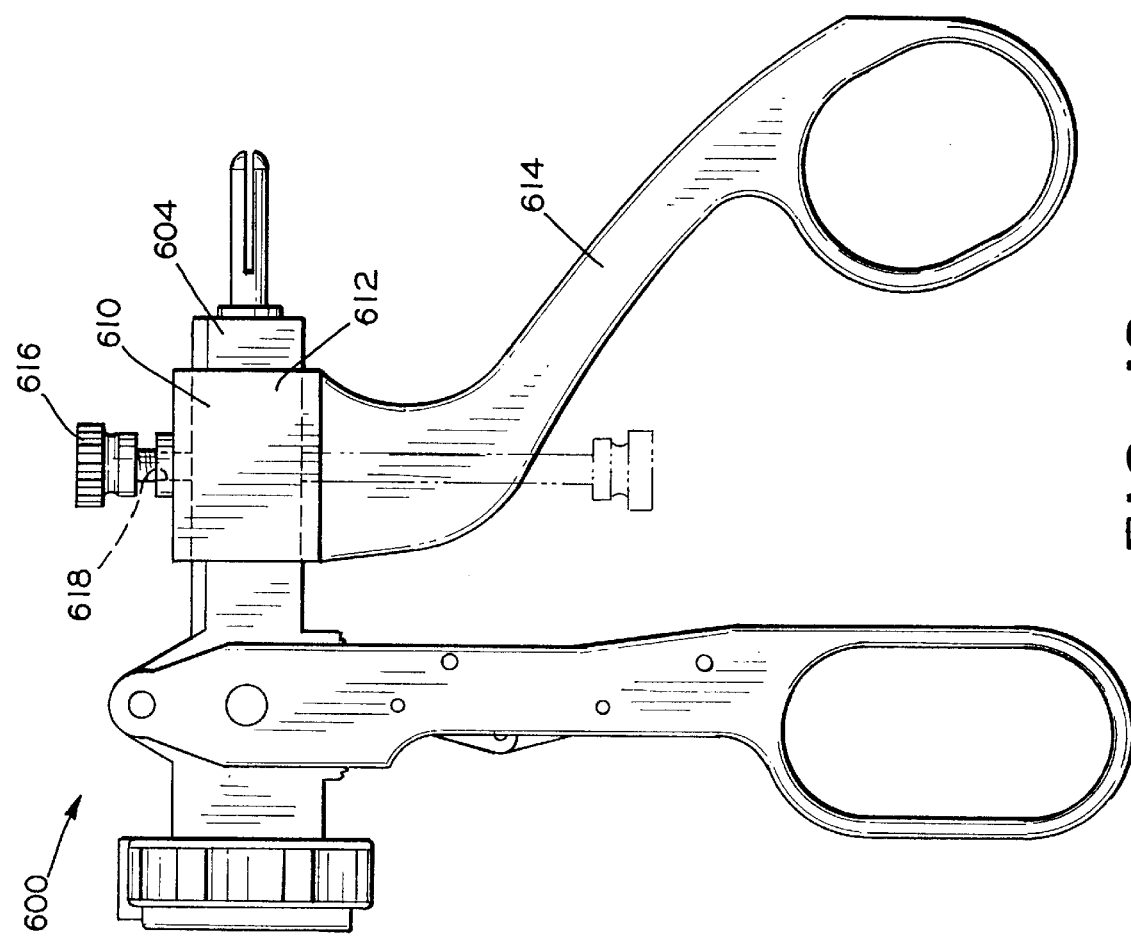
FIG. 18 is a view similar to FIG. 11 showing a sixth embodiment of the instrument of this invention, showing a different structure for adjustably mounting the grip portion of the handle portion.

FIGS. 18 and 19 illustrate a sixth embodiment of a laparoscopic surgical instrument in accordance with this invention, which is indicated generally at 600. The instrument 600 is generally similar to the instrument 500 described above, with three exceptions. The proximal end of a receiver portion 604 of the instrument 600 has a generally square cross section, rather than a cylindrical one like the receiver portion 504 described above. The clamp member 610 includes a hollow body 612 also having a generally square cross section loosely conforming to the proximal end of the receiver portion 604. The clamp member 610, and the attached grip portion 614, can thus move longitudinally relative to the receiver portion, but not rotate relative thereto.

Finally, instead of a locking cam similar to the cam 520 described above, the clamp member 610 is provided with a thumb screw 616 for a locking mechanism. The thumbscrew 616 engages a threaded opening 618 in the body 612, and may be selectively screwed inwardly to engage the receiver portion 604 to fix the relative positions of the grip portion 610 and the receiver portion 604. The thumb screw 616 may be selectively loosened to reposition the grip portion 610 on the receiver portion 604.

It will be appreciated that the opening 618 may be provided to mount the thumb screw 616 at other locations on the body 612. For example the thumb screw could be mounted to extend upwardly through the grip portion 614 as shown in phantom line in FIG. 18, or through the side of the body 614, as shown in FIG. 19. It will be appreciated that the locking cams 420 and 520 described above could be mounted to engage the side of their respective receiver portions. However such an arrangement may be less desirable than the designs illustrated and discussed above, since such an arrangement would likely be less ambidextrous than the discussed designs.

Figure 20:
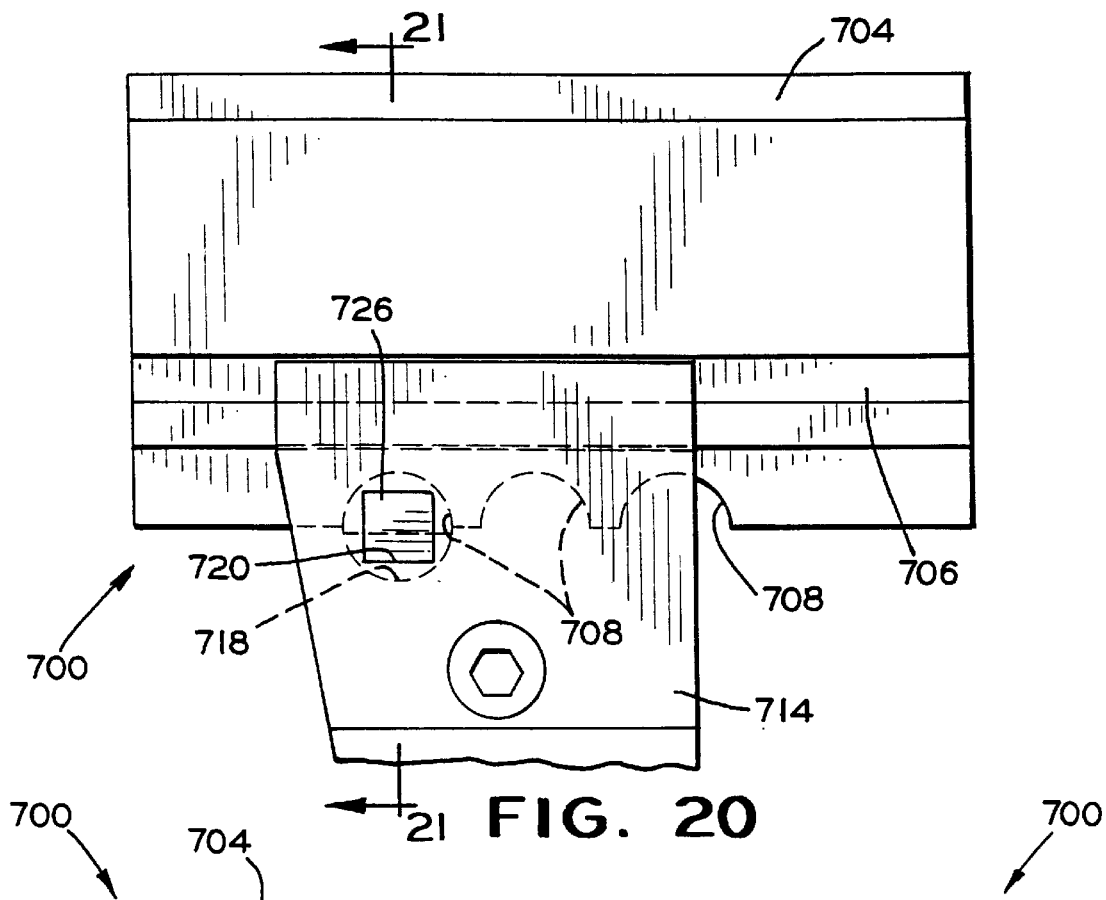
FIG. 20 is a view similar to FIG. 15 showing a seventh embodiment of the instrument of this invention, showing a different structure for adjustably mounting the grip portion of the handle portion.
Figures 21, 22:
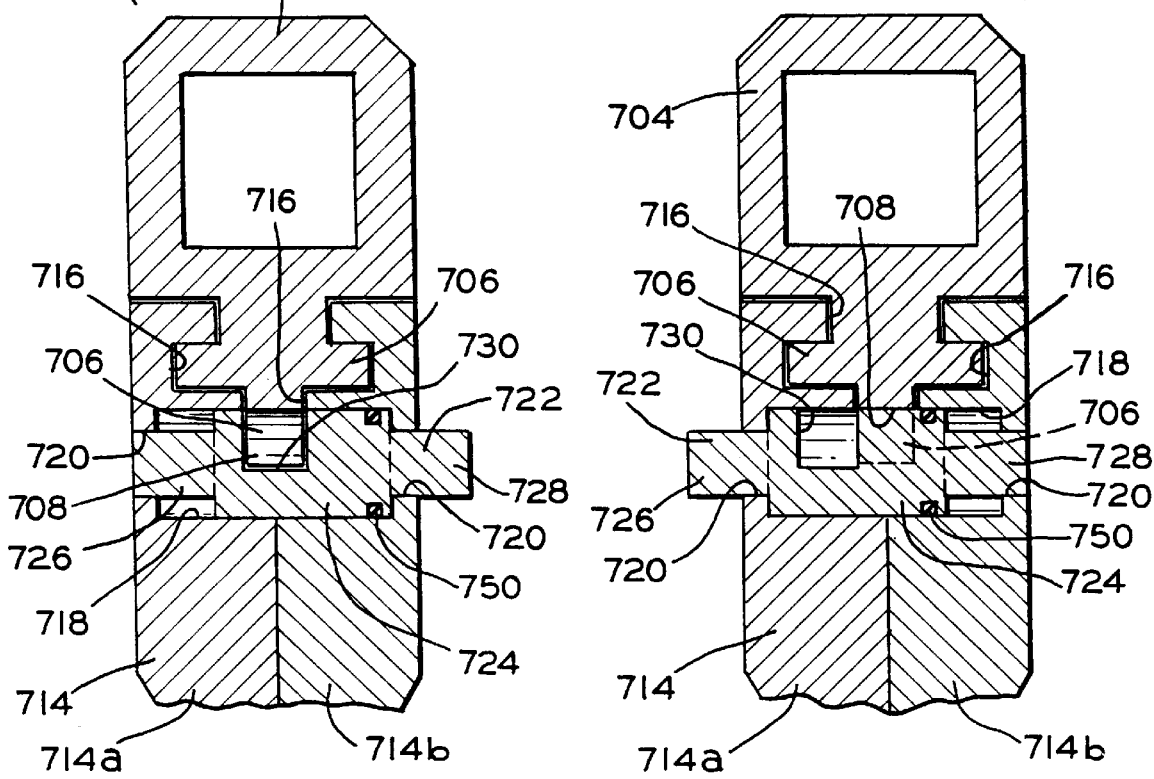
FIG. 21 is a view taken along the line 21—21 of FIG. 20, illustrating the locking mechanism thereof in an unlock condition.
FIG. 22 is a view similar to FIG. 21, illustrating the locking mechanism thereof in an lock condition.

FIGS. 20 through 22 illustrate a seventh embodiment of a laparoscopic surgical instrument in accordance with this invention, which is indicated generally at 700. The instrument 700 is generally similar to the instruments described above which have adjustably mounted grip portions. The proximal end of a receiver portion 704 of the instrument 700 has a longitudinally extending flange 706 depending therefrom. Note that although the receiver portion 704 is shown as a single piece, the receiver portion 704 may suitably be formed from two or more pieces fixed together like, for example, the two symmetrical side pieces forming the receiver portion 304 described above. The flange 706 has a cruciform cross section, as shown in FIGS. 21 and 22. As shown in FIG. 20, the lower portion of the flange 706 is scalloped, having a plurality of recesses 708 extending transversely from side to side of the lower surface of the flange 706. The purpose of the recesses 708 will be described below.

A grip portion 714, formed from a symmetric pair of mating halves 714a and 714b, is slidably mounted on the flange 706. Each of the halves 714a and 714b is formed with respective longitudinally extending recess 716. The recesses 716 cooperate to form a cruciform slot within which the flange 706 is slidably received.

Each half 714a and 714b of the grip portion 714 is formed with a respective cylindrical recess, the two cylindrical recesses cooperating to define a transversely extending cylindrical bore 718 in the grip portion 714. At each end of the cylindrical bore 718, a square opening (or other non-circular opening) 720 extends through the respective half 714a and 714b of the grip portion 714.

A locking pin 722 is slidably disposed within the bore 718. The locking pin 722 has a cylindrical central portion 724. The central portion 724 is shorter in length than the bore 718, so that the locking pin 722 can slide in the bore 718 between a first position, shown in FIG. 21, and a second position, shown in FIG. 22. A pair of extensions 726 and 728 are formed on respective ends of the central portion 724. The extensions 726 and 728 have square cross sections, and extend into respective ones of the openings 720. The openings 720 cooperate with the extensions 726 and 728 to prevent the locking pin 722 from rotating within the bore 718. A user of the instrument 700 can move the locking pin 722 transversely to the first position by pressing against the extension 726, which extends outwardly from the grip portion 714 when the locking pin 722 is not in the first position. The user can move the locking pin 722 to the second position by pressing against the extension 728, which extends outwardly from the grip portion 714 when the locking pin is not in the second position.

The central portion 724 of the locking pin 722 has a notch 730 which extends longitudinally (with respect to the axis of the receiver portion 704 of the instrument 700) through the upper part (as viewed in FIGS. 21 and 22) of the central portion 724 of the locking pin 722. When the locking pin 722 is placed in the first position, the notch 730 is aligned with the flange 706, as shown in FIG. 21, and the grip portion 714 may be selectively moved longitudinally along the flange 706.

The grip portion 714 may be selectively locked in place by the user by aligning the locking pin 722 with one of the transverse recesses 708 formed in the flange 706, and then pressing the extension 728 to move the locking pin to the second position shown in FIG. 22. An unnotched upper part of the central portion 724 of the locking pin 722 is moved into the selected one of the recesses 708, thereby preventing longitudinal movement of the grip portion 714 relative to the receiver portion 704. To unlock the grip portion 714, the user presses against the extension 726, moving the locking pin 722 back to the first position, and aligning the notch 730 with the flange 706. With the notch 730 of the locking pin 722 aligned with the flange 706, the portions of the flange 706 between the recesses 708 slide through the notch 730.

The locking pin 722 will preferably fit within the bore 718 with a tight sliding fit, so that friction will hold the locking pin 722 in the position selected by the user. However, if necessary the locking pin 722 can be provided with a circumferentially extending groove within which an O-ring 750 is mounted. The O-ring 750 is compressed between the locking pin 722 and the wall of the bore 718 to increase the friction therebetween.

It will be understood that the locking mechanism may be formed with a locking pin which prevents relative movement between the grip portion 714 and the receiver portion 704 in other ways than described above. For example, if a locking pin were provided with an enlarged head (not shown) extending from one end thereof, the locking pin could be moved between a first, unlocked position and a second, locked position by manipulating only the enlarged head. Such a locking pin need not extend completely through the receiver portion 704, but could engage a selected one of a plurality of recesses (not shown) formed on an adjacent side of the flange 706. Such recesses could extend completely through the flange 706 to form bores (not shown) in which such a locking pin could be selectively inserted.

FIGS. 23 through 28 illustrate an eighth embodiment of a laparoscopic surgical instrument according to the invention and indicated generally at 800. A handle portion 802 of the instrument 800 is provided with a grip portion 804 which is adjustably mounted on a receiver portion 806. The receiver portion 806 has a depending flange 808, similar to the flange 308, which has a T-shaped cross section and which cooperates with longitudinally extending recesses (not shown, but similar to the recesses 318a and 318b described above) to adjustably mount the grip portion 804 on the receiver portion 806.

Figure 24:
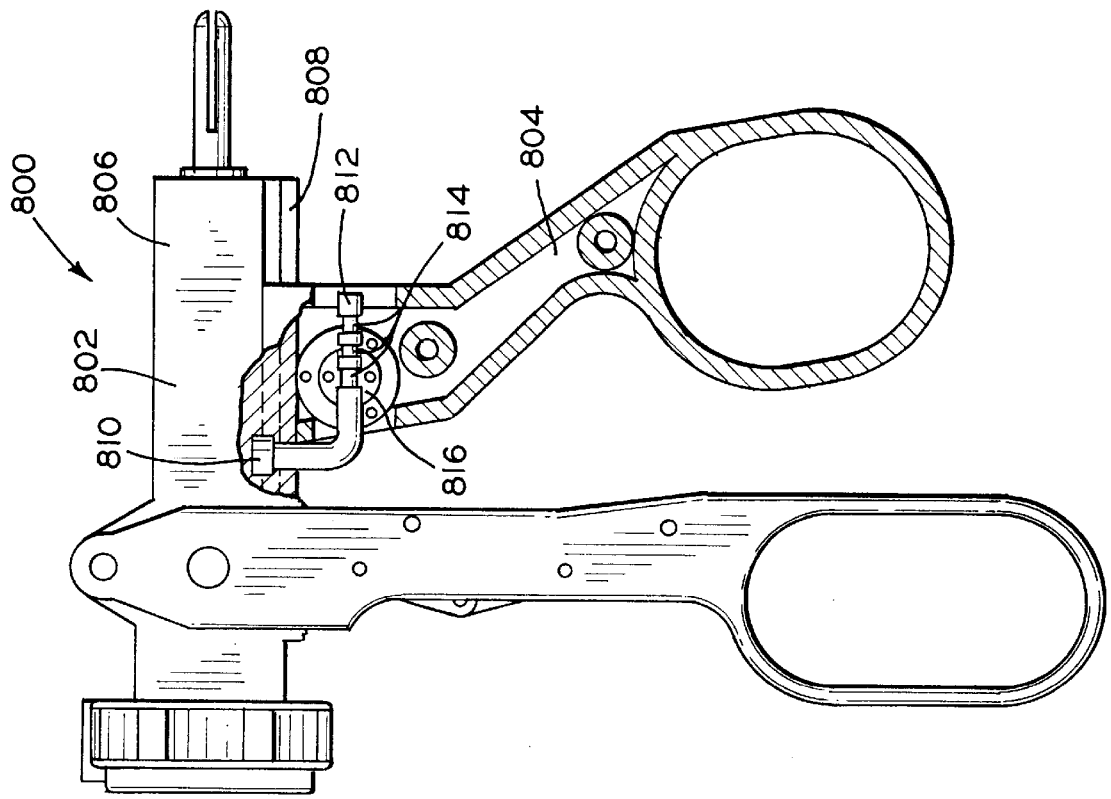
FIG. 24 is a view similar to that of FIG. 23, partly broken away to illustrate the locking mechanism thereof.
Figure 23:
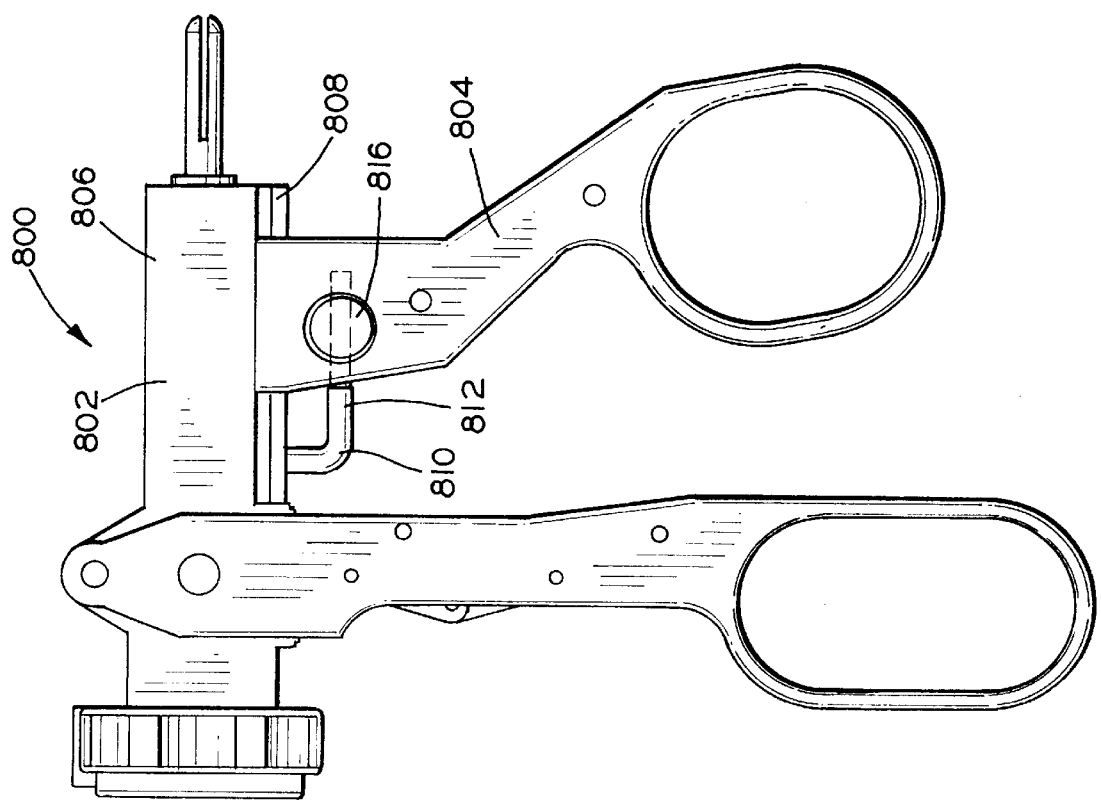
FIG. 23 is a side elevation view of an eighth embodiment of the instrument of this invention, showing a different structure for adjustably mounting the grip portion of the handle portion.

An L-shaped locating pin 810 is fixed to the receiver portion 806. The locating pin 810 has a notched portion 812 which extends parallel to the flange 808. The notched portion 812 of the locating pin 810 has a plurality of circumferentially extending notches 814 formed thereon, as best seen in FIGS. 24 and 25.

The grip portion 804 is provided with a locking mechanism 816 for selectively engaging the notches 814 on the locating pin 810, thereby selectively fixing the relative positions of the grip portion 804 and the receiver portion 806. The locking mechanism 816 may be easily operated by the user of the instrument 800 to disengage the notches 814 to permit the grip portion 804 to be moved longitudinally on the flange 808 to a suitable position relative to the receiver portion 806.

As best seen in FIGS. 25 through 28, the latch mechanism 816 includes two parallel disks 820 and 822. The disks 820 and 822 are arranged in the grip portion 804 on either side of the locating pin 810. The disks 820 and 822 are identical, and the reference numbers assigned to features on the disk 822 described below will also be used to indicated corresponding features on the disk 820.

A finger pad 824 is formed on the outer surface of the disk 822. Three spring retaining pins 826 are fixed to the inner surface of the disk 822 and extend perpendicularly therefrom, the pins 826 being equally spaced about the periphery of the inner surface of the disk 822. A grasper attachment pin 828 is fixed to the inner surface disk 822, and extends perpendicularly therefrom.

A coil spring 830 is seated about each of the spring retaining pins 826 on the disks 820 and 822. The springs 830 act to urge the disks 820 and 822 apart.

A disk shaped grasper plate 832 is operatively coupled to the disk 822, and another grasper plate 834, identical to the plate 832, is operatively coupled to the disk 820 for movement therewith. Each of the plates 832 and 834 is provided with a longitudinally extending groove 836 on the inner surface thereof.

The plate 832 has a first bore 838 formed therethrough into which the grasper attachment pin 828, extending from the disk 822, is fixed, such as by pressing. The grasper attachment pin 828 couples the plate 832 and the disk 822 with the inner face of the plate 832 facing the inner face of the disk 822. The plate 834 has a similar first bore 840 formed therethrough. The associated grasper attachment pin 828 is fixed in the bore 840 to couple the plate 834 and the disk 820 with the inner face of the plate 834 facing the disk 820.

The plate 832 has a second bore 842, of slightly greater diameter than the first bores 838 and 840. The grasper attachment pin 828 coupling the plate 834 to the disk 820 is slidably disposed within the second bore 842. Similarly, the plate 834 has a second bore 844, of the same size as the bore 842, through which passes the grasper attachment pin 828 coupling the plate 832 to the disk 822.

Each of the grasper plates 832 and 834 is provided with a longitudinally extending groove 846 formed in the inner face thereof. The grooves 846 each have a semicircular cross section so that when the plates 832 and 834 are pressed against one another, as shown in FIG. 26, the grooves 846 cooperate to form a generally cylindrical bore, within which the locating pin 810 extends. An inwardly extending flange 848 is formed in each of the grooves 846, which as shown in FIG. 25, can be positioned in a manner described below to engage one of the notches 814 of the locating pin 810.

As depicted in FIG. 26, the springs 830 urge the disks 820 and 822 apart. The grasper plates 834 and 832 are coupled to the associated disks 820 and 822, and are thus urged together such that their respective inner faces are in contact. The flange 848 on each of the grasper plates 834 and 832 is held in a selected one of the notches 814 on the locating pin 810.

To move the grip portion 804 relative to the receiver portion 806, the finger pads 824 of the locking mechanism 816 are pressed toward each other by the user, compressing the springs 830. This causes the grasper plates 832 and 834 to be moved apart from one another, as shown progressively in FIGS. 27 and 28. When the flanges 848 are fully disengaged from the notch 814, the grip portion 804 may be moved along the flange 808 to a desired position. When the flanges 848 are next to the notch 814 corresponding to the desired position of the grip portion 804 on the receiver portion 806, the finger pads 824 of the locking mechanism 816 are released. The springs 830 urge the flanges 848 into the selected notch 814. If the finger pads are released in a slightly wrong position, the flanges 848 may engage the locating pin 810 between the notches 814. In this situation, the grip portion 804 may be pushed longitudinally along the flange 808 until the flanges 848 snap into the selected notch 814 under the urging of the springs 830.

Note that it is contemplated that a locating pin (not shown) similar to the locating pin 810 could be fixed to the moveable grip portion 804. Likewise, a locking mechanism (not shown) similar to the locking mechanism 816 could be mounted on the receiver portion 806 and cooperate with the locating pin on the grip portion 804 to selectively prevent movement of the grip portion 804 relative to the receiver portion 806.

FIGS. 29 and 30 illustrate a ninth embodiment of a laparoscopic surgical instrument according to the invention and indicated generally at 900. A handle portion 902 of the instrument 900 is provided with a grip portion 904 which is adjustably mounted on a receiver portion 906. The grip portion 904 has a flange 908 formed thereon. The flange 908 has a T-shaped cross section and cooperates with a mating slot 910 to mount the grip portion 904 on receiver portion 906. The slot 910 extends along a longitudinal axis in the lower surface of the distal end of the receiver portion 906.

Serrated teeth 912 are formed on the underside of each arm of the flange 908 on the grip portion 904, with mating teeth 914 formed on the adjacent surfaces of the slot 910 formed in the receiver portion 906.

A leaf spring 916, or other suitable spring, is fixed to the upper surface of the flange 908, urging the teeth 912 into engagement with the teeth 914. Axial movement of the grip portion 904 on the receiver portion 906 is thereby prevented by the locking mechanism comprised of the spring 916 and the teeth 912 and the teeth 914.

To adjust the position of the grip portion 904 on the receiver portion 906, a user presses the grip portion 904 toward the receiver portion 906, compressing the spring 916, and disengaging the teeth 912 from the teeth 914. While continuing to compress the spring 916, the grip portion 904 may be moved to a desired position on the distal end of the receiver portion 906 and released, causing the teeth 912 and the teeth 914 to mesh to fix the grip portion 904 in the selected position. As the teeth 912 and the teeth 914 mesh, the grip portion 904 may move slightly from the selected position, in order to reach full engagement of the teeth. The amount of this movement is dependent upon the pitch of the teeth 912 and the teeth 914.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A tool for a surgical instrument, comprising:
   a tubular body having axially extending, diametrically opposed first and second yoke arms formed thereon, said first yoke arm and said second yoke arm each having a respective pivot hole formed therethrough;
   a first jaw having a flange portion formed at one end thereof, said flange portion having first and second opposed faces, a recess being formed in said first face of said flange portion of said first jaw, a first pivot pin extending perpendicularly from said second face of said flange portion of said first jaw through said pivot hole in said first yoke arm to pivotally mount said first jaw on said body; and
   a second jaw having a flange portion formed at one end thereof, said flange portion having first and second opposed faces, a connector pin extending perpendicularly from said first face of said flange portion of said second jaw, said connector pin extending into said recess formed in said first face of said flange portion of said first jaw to pivotally couple said first and second jaws, a second pivot pin extending perpendicularly from said second face of said flange portion of said second jaw through said pivot hole in said second yoke arm to pivotally mount said second jaw on said body.

2. The tool defined in claim 1 wherein said connector pin is received in said recess formed in said first face of said flange portion of said first jaw with a snap fit.

3. The tool defined in claim 1 wherein each of said jaws is formed of a plastic material and includes a respective metallic contact member fixed thereto.

4. The tool defined in claim 1, wherein said first and second pivot pins are integrally formed with said first and second jaws, respectively.

5. The tool defined in claim 1, wherein said connector pin is formed integrally with said second jaw.

6. The tool defined in claim 1, wherein said yoke arms are made of plastic.

7. The tool defined in claim 1, wherein each of said first and second jaws have an elongate gripping portion, each of said elongate gripping portions having an electrical contact fixed thereto, said gripping portions adapted to be connected to a source of electrical power.

8. The tool defined in claim 7, wherein said gripping portions are comprised of plastic and are molded about portions of said pair of electrical contacts.

9. A surgical instrument comprising:

a handle having a trigger arm pivotally mounted to said handle;

a shaft portion including:
  a hollow tube having first and second ends, said first end attached to said handle, and
  an actuating member disposed within said tube, said actuating member having first and second ends, said first end being attached to said trigger arm;

a tool including:
  a body having axially extending, diametrically opposed first and second yoke arms formed thereon, said body being to be mounted on said second end of said tube of said shaft portion, said first yoke arm and said second yoke arm each having a respective pivot hole formed therein;
  a first jaw having a flange portion formed at one end thereof, said flange portion having first and second opposed faces, a recess being formed in said first face of said flange portion of said first jaw, a first pivot pin extending perpendicularly from said second face of said flange portion of said first jaw through said pivot hole in said first yoke arm to pivotally mount said first jaw on said body; and
  a second jaw having a flange portion formed at one end thereof, said flange portion having first and second opposed faces, a connector pin extending perpendicularly from said first face of said flange portion of said second jaw, said connector pin extending into said recess formed in said first face of said flange portion of said first jaw to pivotally couple said first and second jaws, a second pivot pin extending perpendicularly from said second face of said flange portion of said second jaw through said pivot hole in said second yoke arm to pivotally mount said second jaw on said body; and first and second connector members, said first connecting member operatively coupling said flange portion of said first jaw to said second end of said actuating member, said second connecting member operatively coupling said flange portion of said second jaw to said second end of said actuating member.

10. The surgical instrument defined in claim 9, wherein said first and second connecting members are comprised of wire.

11. The surgical instrument defined in claim 10, wherein said first and second connecting members are defined by a pair of end portions of a single length of wire.

12. The surgical instrument defined in claim 9, wherein said body of said tool has a threaded portion cooperating with a mating threaded portion formed on said tube of said shaft portion, to mount said tubular body on said tube.

13. The surgical instrument defined in claim 9, wherein said first and second pivot pins are integrally formed with said first and second jaws, respectively.

14. The surgical instrument defined in claim 9, wherein said connector pin is formed integrally with said second jaw.

15. The surgical instrument defined in claim 9, wherein said yoke arms are made of plastic.

16. The surgical instrument defined in claim 9, wherein each of said first and second jaws have an elongate gripping portion, each of said elongate gripping portions having an electrical contact fixed thereto, said gripping portions adapted to be connected to a source of electrical power.

17. The surgical instrument defined in claim 16, wherein said gripping portions are comprised of plastic and are molded about portions of said pair of electrical contacts.

\* \* \* \* \*

UNITED STATES PATENT AND TRADEMARK OFFICE
CERTIFICATE OF CORRECTION

PATENT NO. : 5,843,122
DATED : December 1, 1998
INVENTOR(S) : EROL D. RIZA

It is certified that error appears in the above-identified patent and that said Letters Patent is hereby corrected as shown below:

Column 26, Claim 1, line 9, after "pivot" change "pin" to --hole--.
Column 27, Claim 9, line 13, after "being" delete --to be--.

Signed and Sealed this

Eleventh Day of May, 1999

Attest:

Q. TODD DICKINSON

*Attesting Officer*    *Acting Commissioner of Patents and Trademarks*